US010863730B2

(12) United States Patent
Ueda et al.

(10) Patent No.: US 10,863,730 B2
(45) Date of Patent: Dec. 15, 2020

(54) GENE KNOCKOUT METHOD

(71) Applicant: RIKEN, Saitama (JP)

(72) Inventors: Hiroki Ueda, Saitama (JP); Genshiro Sunagawa, Saitama (JP); Kenta Sumiyama, Saitama (JP); Maki Ukai, Saitama (JP); Dimitri Perrin, Saitama (JP)

(73) Assignee: RIKEN, Saitama (JP)

( * ) Notice: Subject to any disclaimer, the term of this patent is extended or adjusted under 35 U.S.C. 154(b) by 0 days.

(21) Appl. No.: 15/538,554

(22) PCT Filed: Dec. 25, 2015

(86) PCT No.: PCT/JP2015/086259
§ 371 (c)(1),
(2) Date: Jun. 21, 2017

(87) PCT Pub. No.: WO2016/104716
PCT Pub. Date: Jun. 30, 2016

(65) Prior Publication Data
US 2018/0020646 A1    Jan. 25, 2018

(30) Foreign Application Priority Data
Dec. 26, 2014 (JP) ................. 2014-265793

(51) Int. Cl.
*A01K 67/027* (2006.01)
*C12N 15/873* (2010.01)
*C12N 15/11* (2006.01)
*C12N 15/87* (2006.01)

(52) U.S. Cl.
CPC ........ *A01K 67/0276* (2013.01); *A01K 67/027* (2013.01); *C12N 15/11* (2013.01); *C12N 15/87* (2013.01); *C12N 15/873* (2013.01); *A01K 2207/05* (2013.01); *A01K 2217/075* (2013.01); *C12N 2310/20* (2017.05)

(58) Field of Classification Search
CPC .............. A01K 67/0276; A01K 67/027; A01K 2207/05; A01K 2217/075; C12N 15/11; C12N 15/87; C12N 15/873; C12N 2310/20
See application file for complete search history.

(56) References Cited

U.S. PATENT DOCUMENTS

2016/0186208 A1 * 6/2016 Jaenisch .............. C12N 15/907
800/18

FOREIGN PATENT DOCUMENTS

WO    2014/172470    10/2014
WO    2014/197748    12/2014

OTHER PUBLICATIONS

Sakuma et al. "Multiplex genome engineering in human cells using all-in-one CRISPR/Cas9 vector system." Scientific Reports vol. 4, Article No. 5400 (2014) (Year: 2014).*
Xu et al. "Delivery methods for CRISPR/Cas9 gene editing in crustaceans." Marine Life Science & Technology vol. 2, pp. 1-5(2020) (Year: 2020).*
Kang et al. "CRISPR/Cas9-mediated genome editing in nonhuman primates." Dis Model Mech. Oct. 1, 2019; 12(10) (Year: 2018).*
Xie et al. "Boosting CRISPR/Cas9 multiplex editing capability with the endogenous tRNA-processing system." PNAS Mar. 17, 2015 112 (11) 3570-3575 (Year: 2015).*
Peng et al. "Potential pitfalls of CRISPR/Cas9-mediated genonne." FEBS J. Apr. 2016;283(7):1218-31. (Year: 2016).*
McCarty et al. "Multiplexed CRISPR technologies for gene editing and transcriptional regulation." Nature Communications vol. 11, Article No. 1281 (2020) (Year: 2020).*
Sakuma T. et al., Multiplex genome engineering in human cells using all-in-one CRISPR/Cas9 vector system, Sci Rep., Jun. 23, 2014, 4, 5400, p. 1-6.
Wang H. et al., One-step generation of mice carrying mutations in multiple genes by CRISPR/Cas-mediated genome engineering, Cell, May 9, 2013, 153(4), p. 910-918, Epub May 2, 2013.
International preliminary report on patentability of International Application No. PCT/JP2015/086259, dated Jul. 6, 2017.
International Search Report of International Application No. PCT/JP2015/086259, dated Mar. 22, 2016.
Zhou, Jiankui et al: "Dual sgRNAs facilitate CRISPR/Cas9-mediated mouse genome targeting", FEBS Journal, vol. 281, No. 7, Feb. 26, 2014 (Feb. 26, 2014), pp. 1717-1725.
Fujii, W. et al: "Efficient generation of large-scale genome- . . . ", Nucleic Acids Research, vol. 41, No. 20, Aug. 30, 2013 (Aug. 30, 2013).
Piatek, Agnieszka et al: "RNA-guided transcriptional regulation in planta via synthetic dCas9-based transcription factors", Plant Biotechnology Journal, vol. 13, No. 4, Nov. 14, 2014 (Nov. 14, 2014), pp. 578-589.

(Continued)

*Primary Examiner* — Titilayo Moloye
(74) *Attorney, Agent, or Firm* — Casimir Jones, S.C.; Tanya A. Arenson

(57) ABSTRACT

A method for producing a cell in which a target gene is knocked out, the method including the step of: introducing a CRISPR-Cas system into a cell having one or more kinds of target genes, the CRISPR-Cas system being able to produce (i) three or more kinds of guide RNAs for each of the one or more kinds of target genes and (ii) a Cas protein. The present invention can provide a method that enables highly efficient (90% or more) production of whole-body biallelic knockout animals in a single generation.

3 Claims, 12 Drawing Sheets

Specification includes a Sequence Listing.

(56) References Cited

OTHER PUBLICATIONS

Sunagawa, Genshiro A. et al: "Mammalian Reverse Genetics without Crossing Reveals Nr3a as a Short-Sleeper Gene", Cell Reports, vol. 14, No. 3, Jan. 1, 2016 (Jan. 1, 2016), pp. 662-677.
EP Search Report, EP Patent Application No. 15873284.2, dated May 11, 2018, 9 pages.
Zhaoyu Xue, CRISPR/Cas9 Mediates Efficient Conditional Mutagenesis in *Drosophila*, G3, Sep. 5, 2014, vol. 4, pp. 2167-2173, Supporting information.
Office Action for JP Patent Application No. 2016-566520, dated Oct. 23, 2019, 11 pages.

* cited by examiner

SEQUENCE LISTING

```
<160> NUMBER OF SEQ ID NOS: 39

<210> SEQ ID NO 1
<211> LENGTH: 25
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 1
gtaaaatcga taaggatccg tcgac                                           25

<210> SEQ ID NO 2
<211> LENGTH: 60
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 2
cagctgaaac tgcagaaaga tatcaaagaa ttcttaatcc agatccacaa ccttcgcttc     60

<210> SEQ ID NO 3
<211> LENGTH: 52
<212> TYPE: DNA
<213> ORGANISM: Artificial Sequence
<220> FEATURE:
<223> OTHER INFORMATION: Description of Artificial Sequence:
      oligonucleotide
```

-continued

<210> SEQ ID NO 3
<211> LENGTH: 52
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 3
gatatctttc tgcagtttca gctgccaatc atccaaaaaa ttattatcat gg    52

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 4
catcggtcga cggatcctta tcg    23

<210> SEQ ID NO 5
<211> LENGTH: 36
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 5
taagaattct ttgatatctt tctgcagttt cagctg    36

<210> SEQ ID NO 6
<211> LENGTH: 27
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 6
ggcacctatg gccaaatgaa caatggg    27

<210> SEQ ID NO 7
<211> LENGTH: 30
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 7
gttcccacaa taacaagaaa agtctgtgcc    30

<210> SEQ ID NO 8
<211> LENGTH: 25
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 8
tggaacaagc cagtcgtatc tggcc    25

<210> SEQ ID NO 9
<211> LENGTH: 28
<212> TYPE: DNA
<213> ORGANISM: Artificial Sequence
<220> FEATURE:
<223> OTHER INFORMATION: Description of Artificial Sequence:
      oligonucleotide

```
<400> SEQUENCE: 9
tcacagatgg ctctgataca gcaagctg                                      28

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 10
caccgtgtca agggacacac tgct                                          24

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 11
aaacagcagt gtgtcccttg acac                                          24

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 12
caccgttatt gctgcagctc tctc                                          24

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 13
aaacgagaga gctgcagcaa taac                                          24

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 14
caccgaagaa gaagcaaccc cagg                                          24

<210> SEQ ID NO 15
<211> LENGTH: 24
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 15
```

```
aaaccctggg gttgcttctt cttc                                            24
```

<210> SEQ ID NO 16
<211> LENGTH: 48
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 16

```
cactataggg acctcagttc cccttcaagt tttagagcta gaaatagc                  48
```

<210> SEQ ID NO 17
<211> LENGTH: 44
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 17

```
gggcctaata cgactcacta tagggacctc agttccccctt caag                     44
```

<210> SEQ ID NO 18
<211> LENGTH: 48
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 18

```
cactataggg tttgacccag tatgaatcgt tttagagcta gaaatagc                  48
```

<210> SEQ ID NO 19
<211> LENGTH: 44
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 19

```
gggcctaata cgactcacta tagggtttga cccagtatga atcg                      44
```

<210> SEQ ID NO 20
<211> LENGTH: 48
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 20

```
cactatagga gtctctgtta tggccgatgt tttagagcta gaaatagc                  48
```

<210> SEQ ID NO 21
<211> LENGTH: 44
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 21

```
gggcctaata cgactcacta taggagtctc tgttatggcc gatg              44
```

<210> SEQ ID NO 22
<211> LENGTH: 48
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 22

```
cactataggg tcatccaccc ctttgaaggt tttagagcta gaaatagc          48
```

<210> SEQ ID NO 23
<211> LENGTH: 44
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 23

```
gggcctaata cgactcacta tagggtcatc caccctttg aagg              44
```

<210> SEQ ID NO 24
<211> LENGTH: 48
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 24

```
cactataggt gttgacccat tgttcattgt tttagagcta gaaatagc          48
```

<210> SEQ ID NO 25
<211> LENGTH: 44
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 25

```
gggcctaata cgactcacta taggtgttga cccattgttc attg              44
```

<210> SEQ ID NO 26
<211> LENGTH: 48
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 26

```
cactatagga gccatggcca gatacgacgt tttagagcta gaaatagc          48
```

<210> SEQ ID NO 27
<211> LENGTH: 44
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 27

```
gggcctaata cgactcacta taggagccat ggccagatac gacg              44
```

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 28
aaaagcaccg actcggtgcc                                              20

<210> SEQ ID NO 29
<211> LENGTH: 43
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 29
gggcctaata cgactcacta taggtgtcaa gggacacact gct                    43

<210> SEQ ID NO 30
<211> LENGTH: 43
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 30
gggcctaata cgactcacta taggttattg ctgcagctct ctc                    43

<210> SEQ ID NO 31
<211> LENGTH: 43
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 31
gggcctaata cgactcacta taggaagaag aagcaacccc agg                    43

<210> SEQ ID NO 32
<211> LENGTH: 23
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 32
gtgtcaaggg acacactgct tgg                                          23

<210> SEQ ID NO 33
<211> LENGTH: 23
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 33
ctgtgccaag gcagaaaccc tgg                                          23

```
<210> SEQ ID NO 34
<211> LENGTH: 23
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 34
gttattgctg cagctctctc tgg                                              23

<210> SEQ ID NO 35
<211> LENGTH: 24
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 35
gtctttgtcc atgaggagtg gctg                                             24

<210> SEQ ID NO 36
<211> LENGTH: 23
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 36
gttattgctg cagctctctc tgg                                              23

<210> SEQ ID NO 37
<211> LENGTH: 25
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 37
tcacagatgg ctctgataca gcaag                                            25

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 38 cccctctgc actgaaatca                                                   20

<210> SEQ ID NO 39
<211> LENGTH: 21
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 39
gtagcagcac agagcaagca a                                                21
```

GENE KNOCKOUT METHOD

TECHNICAL FIELD

The present application claims priority on Japanese Patent Application, Tokugan, No. 2014-265793 filed on Dec. 26, 2014, the entire contents of the specification of which are hereby incorporated by reference.

The present invention relates to a method for knocking out a gene, for example, a method for producing a knock-out animal in which a certain gene function is deleted.

BACKGROUND ART

The system-level identification of molecular networks in organisms is an important challenge in biology. Classical reverse genetics requires several generations of animal crosses to produce mutant animals of sufficient quality and quantity for phenotype analysis. Conventional methods for producing knockout mice ordinarily involve targeting-vector construction (approximately 2 weeks), introduction of target mutations into embryonic stem (ES) cells by homologous recombination (2 weeks to 3 weeks) and injection of the mutant ES cells into wild-type blastocysts to produce chimeric mice (3 weeks). If the mutant ES cells contribute to the germ-line of the newborn chimeric mice, their next-generation offspring will possess a heterozygous mutation (approximately 3 months). Further crossings of the offspring (several months to years; at least 3 months per generation) will produce mice with completely homozygous knockout mutations on an inbred genomic background, which is required for reliable phenotype analysis. Therefore, conventional methods require substantial amounts of time, space, effort to knock out even a single gene. Therefore, identification of molecular networks comprehensively in organisms requires genetic alterations without crossing. In order to attain this goal, efficient (>90%) mutant production in a single generation and accurate (>90%) phenotype analyses of mutant animals are both needed.

The efficient production of mice in which two alleles are knocked out (hereinafter also referred to as "biallelic knock-out mice") can be facilitated by recently developed genome editing techniques, such as ZFNs (zinc-finger nucleases) (Non-Patent Literature 1), TALENs (transcription activator-like effector nucleases) (Non-Patent Literature 2), and the CRISPR/Cas nuclease systems (hereinafter also referred to as "CRISPR/Cas system" or "CRISPR-Cas system") (Non-Patent Literatures 3 and 4). Unlike the protein-based ZFNs and TALENs, the CRISPR/Cas system uses RNA-based DNA recognition derived from a bacterial adaptive immune system (Non-Patent Literatures 5 and 6). This method achieves production of knockout animals via co-injection, into embryos, of (i) Cas9 protein or expression vectors or RNAs encoding the Cas9 protein and (ii) target-locus-specific guide RNAs (gRNAs) or expression vectors encoding the gRNA (Non-Patent Literatures 4 and 7). Patent Literature 1 discloses a method for specifically cutting a target sequence by introducing, into a cell, (i) guide RNAs designed based on the target sequence and (ii) RNAs encoding a Cas protein. Several modifications of the CRISPR/Cas9 system have been also introduced to improve the efficiency and specificity of targeted mutations in a genome (Non-Patent Literatures 8 through 10).

CITATION LIST

Non-Patent Literatures

[Non-patent Literature 1]
Carbery, I. D. et al., (2010). Targeted genome modification in mice using zinc-finger nucleases. Genetics 186, 451-459.
[Non-patent Literature 2]
Sung, Y. H. et al., (2013). Knockout mice created by TALEN-mediated gene targeting. Nature biotechnology 31, 23-24
[Non-patent Literature 3]
Hsu, P. D. et al., (2014). Development and applications of CRISPR-Cas9 for genome engineering. Cell 157, 1262-1278.
[Non-patent Literature 4]
Wang, H. et al., (2013). One-step generation of mice carrying mutations in multiple genes by CRISPR/Cas-mediated genome engineering. Cell 153, 910-918.
[Non-patent Literature 5]
Horvath, P., and Barrangou, R. (2010). CRISPR/Cas, the immune system of bacteria and archaea. Science (New York, N.Y.) 327, 167-170.
[Non-patent Literature 6]
Wiedenheft, B. et al., (2012). RNA-guided genetic silencing systems in bacteria and archaea. Nature 482, 331-338.
[Non-patent Literature 7]
Fujii, W. et al., (2013). Efficient generation of large-scale genome-modified mice using gRNA and CAS9 endonuclease. Nucleic acids research 41, e187.
[Non-patent Literature 8]
Fu, Y. et al., (2014). Improving CRISPR-Cas nuclease specificity using truncated guide RNAs. Nature biotechnology 32, 279-284.
[Non-patent Literature 9]
Ran, F. A. et al., (2013) Genome engineering using the CRISPR-Cas9 system. Nature protocols 8, 2281-2308.
[Non-patent Literature 10]
Zhou, J. et al., (2014). Dual sgRNAs facilitate CRISPR/Cas9-mediated mouse genome targeting. The FEBS journal 281, 1717-1725.

PATENT LITERATURE

[Patent Literature 1]
PCT International Publication, No. WO/2014/093661 (Publication Date: Jun. 19, 2014)

SUMMARY OF INVENTION

Technical Problem

As described above, the CRISPR/Cas system is promising as a method for efficiently generating biallelic knockout mice. However, the following two problems remain: 1) first-generation mice often contain a mosaic of wild-type and knockout cells, and 2) the rate of complete biallelic mutant mice produced is relatively low (ordinarily approximately 60% to 80%). For example, although Non-Patent Literature 10 reports the use of two guide RNAs for a single target gene, knockout efficiency is low such as less than 80%. This indicates that phenotype observation without crossings is not possible. Therefore, it is an object of the present invention to provide a method that enables highly efficient (90% or more) production of whole-body biallelic knockout animals in a single generation.

Solution to Problem

As a result of diligent study to attain the object, the inventors of the present invention achieved extremely high knockout efficiency (approximately 100%) by use of three kinds of guide RNAs with respect to a single target gene. Consequently, the inventors of the present invention found that a resulting animal can be subjected to a phenotype observation test in "a single generation" without a crossing or selection. According to the conventional methods for producing knockout mice, it is necessary to perform procedures such as: establishing ES cell lines into which vector having been constructed in advance are introduced; producing chimeric mice through injection of ES cells into blastocysts of the mice, and obtaining homozygous knockout mice by mating of the chimeric mice. This causes establishment of a strain to require a long period of time (approximately one year). However, with the method in accordance with an embodiment of the present invention, it is possible to design and synthesize guide RNA, inject the guide RNA into fertilized eggs, and use resulting mice directly. This allows intended mice to be obtained in such a short period of time as approximately one month.

Specifically, the present invention provides the following: (1) A method for producing a cell in which a target gene is knocked out, the method including the step of: introducing a CRISPR-Cas system into a cell having one or more kinds of target genes, the CRISPR-Cas system being able to produce (i) three or more kinds of guide RNAs for each of the one or more kinds of target genes and (ii) a Cas protein.

Advantageous Effects of Invention

With the present invention, highly efficient production of whole-body biallelic knockout animals in a single generation is possible. With the present invention, extremely high knockout efficiency can be achieved. This allows a resulting animal to be subjected to a phenotype observation test in a single generation without a crossing or selection.

DESCRIPTION OF EMBODIMENTS

Figure 1:
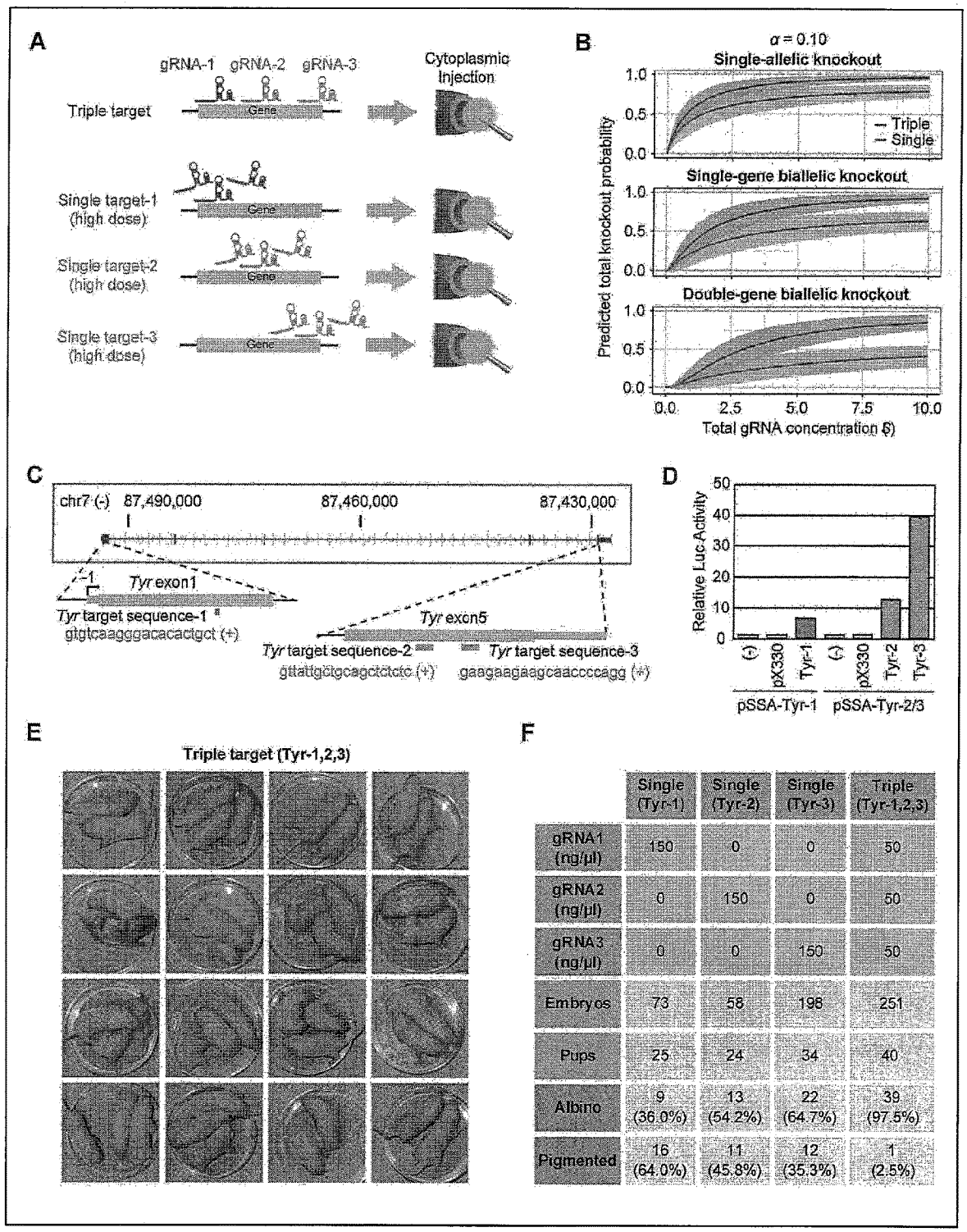
FIG. 1 illustrates a triple-target CRISPR method (knockout method by CRISPR using three kinds of guide RNAs) for highly efficient production of whole-body biallelic knockout mice.

The following description will discuss the present invention in more detail.

A method in accordance with an embodiment of the present invention for knocking out a target gene in a cell is a method including the step of: introducing a CRISPR-Cas system into a cell having one or more kinds of target genes, the CRISPR-Cas system being able to produce (i) three or more kinds of guide RNAs for each of the one or more kinds of target genes and (ii) a Cas protein. In an embodiment of the present invention, the one or more kinds of target genes are knocked out by (i) causing three or more kinds of guide RNAs to target each of the one or more kinds of target genes and then (ii) causing a Cas protein to cut each of the one or more kinds of target gene.

CRISPR (Clustered Regularly Interspaced Short Palindromic Repeat) includes several tens of base pairs of short repetitive sequence and is a locus serving as a type of acquired immune system in a prokaryote. It is known that a CRISPR-associated (cas) gene cluster encoding nuclease and helicase exists in the vicinity of a CRISPR repetitive sequence. Foreign DNA is fragmented, by protein encoded by any cas gene cluster, into a length of approximately 30 base pairs. In a case where it is inserted into the CRISPR locus by any method, the fragments function as immunological memory. At the CRISPR locus, RNA is transcribed, so that RNA is fragmented by Cas protein into smaller RNAs (crRNAs) having respective foreign sequences. The RNA guides another Cas protein to the foreign DNA (or RNA derived from the foreign DNA), so that a mechanism similar to RNAi of a eukaryote suppresses the function of the foreign DNA (or RNA derived from the foreign DNA). The CRISPR-Cas system is applied to RNA-guided genomic engineering at a cellular level or an individual level.

The CRISPR-Cas system will be described below. crRNA, which is complementary to a target DNA in a target gene intended to be cut, and tracrRNA (trans-activating crRNA) are fused via a linker, so that chimeric tracrRNA-crRNA is produced. This chimeric tracrRNA-crRNA will be referred to as guide RNA (gRNA).

The length of the target DNA in the target gene is at least any one of 15 nucleotides, 16 nucleotides, 17 nucleotides, 18 nucleotides, 19 nucleotides, 20 nucleotides, and 25 nucleotides, and can be, for example, 10 nucleotides to 30 nucleotides, 15 nucleotides to 25 nucleotides, or 15 nucleotides to 20 nucleotides. This allows nuclease (RNA-guided nuclease; RGN) to be recruited, so that it is possible to cut the target DNA at an intended site. There are type I, type II, and type III of CRISPR/Cas. The type mainly used in genome editing is type II CRISPR/Cas. In the type II, Cas9 is used as RGN. Cas9 of *Streptococcus pyogenes* recognizes three bases, NGG, as Proto-spacer Adjacent Motif (PAM). Therefore, a sequence in which two guanines are adjacent can be cut at the upstream thereof. This makes it possible to target any one of substantially all of DNA sequences on a genome.

A method in which CRISPR/Cas is used allows, only by synthesis of short gRNA homologous with a target DNA sequence as described above, editing of a genome with use of Cas protein which is a single protein. Therefore, unlike ZFN (Zinc Finger Nuclease) or TALEN (Transcription Activator-Like Effector Nuclease) previously developed, it is unnecessary to synthesize large proteins that vary depending on DNA sequences. This advantageously allows simple and prompt genome editing.

An embodiment of the present invention is characterized by use of three or more kinds of guide RNAs for each kind of target gene (i.e. use of guide RNAs having sequences which are complementary to respective three or more kinds of target DNAs in a single target gene). Note that there is no particular upper limit to the number of kinds of guide RNAs, provided that three or more kinds of guide RNAs are used for each kind of target gene. It is possible to use four, five, or more kinds of guide RNAs. It is preferable to use three kinds of guide RNAs.

Guide RNAs preferably satisfy at least one (particularly preferably all) of the following conditions.
(1) No exact matches at a plurality of parts in a genome.
(2) A target is neither: (i) a target with a low AT percentage (below 45%), which has a risk of binding strongly to an off-target site (a site other than an intended sequence in a target gene) nor (ii) a target that contains TTTT, which tends to loosen the gRNA's secondary structure.

(3) A target is not excessively similar to a reverse primer (Wang, H., et al., (2013). One-step generation of mice carrying mutationsin multiple genes by CRISPR/Cas-mediated genome engineering. Cell 153, 910-918) in a case where PCR-based synthesis of gRNA template is performed with use of pX330 as template.

(4) A candidate for which a stem loop structure for Cas9 recognition cannot correctly fold is to be eliminated, except in a case where folding energy was above −18 (which indicates that the "wrong" structure was very unstable) as a result of calculation of a secondary structure of gRNA.

(5) A score of an off-target risk evaluated by implementation of the Zhang tool (Non-Patent Literature 9) is 75 or more.

Examples of the Cas protein encompass, but are not particularly limited to, CAS1, CAS1B, CAS2, CAS3, CAS4, Cas5, Cas6, Cas7, Cas8, Cas9, Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, a homologue thereof, and a mutant thereof. These enzymes are publicly known. The Cas protein is particularly preferably a Cas9 protein.

Components constituting the CRISPR-Cas system are not limited to any particular ones, provided that guide RNAs and Cas protein can be produced in a cell.

Examples of a manner in which guide RNA can be produced encompass (i) a form in which a guide RNA itself is introduced as RNA into a cell and (ii) a form in which a vector (such as DNA vector) that can express a guide RNA in a cell is introduced into a cell. In a case where a guide RNA itself is introduced into a cell, for example, a guide RNA can be obtained by chemical synthesis or in vitro transcription of a guide RNA. In a case where a vector that can express a guide RNA in a cell is used, it is preferable to use an expression vector that contains (i) a DNA encoding the guide RNA and (ii) an expression regulatory sequence (such as a promoter) upstream of the DNA.

A vector herein means, but is not limited to, any one of a wide range of nucleic acid molecules which are single-stranded, double-stranded, or partially double-stranded. A vector can be a nucleic acid molecule containing DNA, RNA, or both of DNA and RNA. Specific examples of the vector encompass, but are not particularly limited to, plasmid vectors and virus vectors (such as a retrovirus vector, an adenovirus vector, and an adeno-associated virus vector). The vector can be a vector which is autonomously replicated in a host cell into which the vector is introduced. Alternatively, the vector can be a vector that is integrated into a genome of a host cell when the vector is introduced into the host cell.

Among the CRISPR-Cas systems listed above, the CRISPR-Cas system is preferably a system that includes (i) three or more kinds of guide RNAs for each kind of target gene and (ii) RNA that encodes a Cas protein.

Note that the CRISPR-Cas system used in accordance with an embodiment of the present invention is non-naturally occurring system, and is produced artificially.

Examples of a manner in which a Cas protein can be produced encompass (i) a form in which Cas protein itself is introduced as a protein into a cell, (ii) a form in which RNA encoding a Cas protein is introduced into a cell, and (iii) a form in which a vector (such as DNA vector) that can express a Cas protein in a cell is introduced into a cell. In a case where a vector that can express a Cas protein in a cell is used, it is preferable to use an expression vector that contains (i) a DNA encoding the Cas protein and (ii) an expression regulatory sequence (such as a promoter) upstream of the DNA.

The kind of an expression regulatory sequence to be used in a vector expressing a guide RNA or a Cas protein is not particularly limited. Any expression regulatory sequence functions in a cell into which an expression vector is introduced can be used. Examples of the expression regulatory sequence encompass, but are not particularly limited to, promoters, enhancers, internal ribosome entry sites (IRES), and any other expression regulatory elements (e.g. transcription termination signals such as a polyadenylation signal and a poly(U) sequence). The expression regulatory sequence can be a sequence that induces constitutive expression of genes in a wide range of host cells, or can be a sequence that induces expression of genes in certain host cells. Examples of a tissue-specific promoter that induces expression of gene in only a certain host cell encompass promoters which can induce expression in a desired tissue such as muscle, nerve, bone, skin, blood, certain organs (e.g. liver and pancreas), and certain cell types (e.g. lymphocyte). Specific examples of the promoter encompass, but are not limited to, pol III promoter, pol II promoter, pol I promoter, and a combination thereof. Specific examples of the pol III promoter encompass, but are not limited to, U6 promoter and HI promoter. Examples of the poll promoter encompass, but are not limited to, retrovirus Rous sarcoma VIMS (RSV) LTR promoters, cytomegalovirus (CMV) promoters), SV40 promoters, dihydrofolate reductase promoters, β actin promoters, phospho-glycerol kinase (PGR) promoters, and EFL promoters.

In a case where an expression vector expressing guide RNA or Cas protein is to be used, at least four kinds of DNAs that encode three or more kinds of guide RNAs and a Cas protein can be contained in a single expression vector or contained in respective expression vectors. For example, the following cases are possible:

(1) A case where a single expression vector, which contains all of DNAs encoding three or more kinds of guide RNAs and a Cas protein, is to be used;

(2) A case where an expression vector, which contains all of DNAs encoding three or more kinds of guide RNAs, and an expression vector encoding a Cas protein, are to be used;

(3) A case where three or more kinds of expression vectors, which contain respective three or more kinds of guide RNAs, and an expression vector, which contains DNA encoding a Cas protein, are to be used.

Note, however, the present invention is not particularly limited to these cases.

The type of cell into which the CRISPR-Cas system in accordance with an embodiment of the present invention is to be introduced is not limited to any particular one. The cell can be a prokaryotic cell or a eukaryotic cell, and is preferably a eukaryotic cell, and more preferably an animal cell. The animal cell is particularly preferably a mammal cell (such as a mouse cell or a human cell).

In a case where a knockout animal, in which a gene that is a target gene is knocked out by a method in accordance with an embodiment of the present invention, is to be produced, it is possible to use a fertilized egg as the cell. Production of a knockout animal will be described later.

The CRISPR-Cas system, when introduced into a cell, is not particularly limited in terms of which site of the cell the CRISPR-Cas system is to be introduced. The CRISPR-Cas system can be introduced into a nucleus, or can be introduced into a cytoplasm. In a case where the CRISPR-Cas system is to be introduced in a form of RNA, the CRISPR-Cas system can be introduced into a cytoplasm.

The CRISPR-Cas system can be introduced into a cell by a method such as viral particles, liposome, electroporation, microinjection, and conjugation.

The method of the present invention for knocking out a target gene in a cell can be used for production of a knockout non-human organism, gene therapy, drug screening, and diagnosis and prognosis of a disease. The method is preferably used for production of a knockout non-human organism.

The present invention provides a method for producing a knockout non-human organism, including the steps of: obtaining an embryo in which a target gene has been knocked out by the method of the present invention for knocking out a target gene in a cell; and transplanting the embryo into a pseudopregnant non-human animal, so as to obtain an offspring.

Examples of the non-human organism encompass animals (such as mammals, birds, reptiles, amphibians, and fish), arthropods (such as insects), and plants. Among these, the non-human organism is preferably an animal, more preferably a mammal, and still more preferably a rodent (any one of a mouse, a rat, a hamster, and a rabbit, for example).

The embryo as a target gene is knocked out by the method of the present invention for knocking out a target gene in a cell is preferably a fertilized egg in which a target gene is knocked out by a method for knocking out a target gene in a fertilized egg of a non-human animal. For example, it is possible to produce a knockout non-human animal by (i) incubating, under certain conditions (such as in a 5% $CO_2$ incubator at 37° C.), embryos in each of which Cas9 mRNA and three or more kinds of gRNAs for each kind of target gene were injected into the cytoplasm of a fertilized egg and then (ii) transferring a plurality of embryos (e.g. approximately 15 to 30 embryos) to oviducts of pseudopregnant non-human animals, so as to cause the non-human animals to give birth. In a case where pseudopregnant female mice are used as the pseudopregnant non-human animals, each of the pseudopregnant female mice can be obtained by mating a female mouse of a normal estrus cycle with a male mouse that has been castrated by vasoligation or the like.

In the method of the present invention for producing a knockout non-human organism, (i) target genes are biallelic genes and (ii) a ratio of whole-body biallelic knockout individuals to all of offspring obtained is preferably 90% or more, more preferably 93% or more, still more preferably 95% or more, and particularly preferably 97% or more Still more preferably, (i) target genes are two or more kinds of target genes and (ii) a ratio of whole-body biallelic knockout individuals for each of the two or more kinds of target genes to all of offspring obtained is preferably 90% or more, still more preferably 93% or more, still more preferably 95% or more, and particularly preferably 97% or more.

In accordance with an embodiment of the present invention, the kind of a target gene is not limited to any particular one. Any gene can be selected as a target gene, provided that the gene allows a desired guide RNA to be designed. The target gene is preferably a gene which, when knocked out, causes a change in function of a cell. In a case where a knockout non-human organism is to be produced, a target gene is preferably a gene which, when knocked out, causes a change in phenotype of the individual. In this case, the method of the present invention allows a knockout animal to be obtained highly efficiently. This makes it possible to observe a phenotype in a single generation.

In the present invention, target genes are preferably two or more kinds of target genes, and the two or more kinds of target genes are knocked out by the method in accordance with an embodiment of the present invention.

Specific examples of the target gene encompass, but are not particularly limited to, a disease-associated gene and a signaling pathway-associated gene. Specific examples of the disease-associated gene encompass the genes shown in Table A and Table B of International Publication No. WO2014/093661. Specific examples of the signal-transducing pathway-associated gene encompass the genes shown in Table C of International Publication No. WO2014/093661. The contents of Table A, Table B, and Table C of International Publication No. WO2014/093661 are cited herein.

As mentioned above, the term "knockout" is herein used to indicate disrupting, through cutting of a genome in a cell by the CRISPR-Cas system, a function of a target gene which exists in the genome. Note, however, that as described below, the use of the CRISPR-Cas system allows not only disruption of gene function but also various editing such as modification, activation, and suppression. This allows the present invention to be applied to techniques for any gene editing which can be performed by use of the CRISPR-Cas system. Therefore, the term "knockout" herein encompasses not only disrupting of gene function but also techniques for any gene editing which can be performed by use of the CRISPR-Cas system. As shown in Example, knockout results from random mutation (such as substitution, deletion, and/or insertion) of an original nucleotide sequence of a target gene, which mutation occurs due to cutting of a genome by the CRISPR-Cas system. That is, the type of the mutation (e.g. nucleotide sequence to be inserted or substituted in a case where insertion and substitution occur) is not artificially selected.

Meanwhile, it is well-known art in the field that the function of a target gene can be disrupted by inserting, into a gene that has been cut, a foreign nucleotide sequence which has been artificially selected. The nucleotide sequence is a functional gene or a non-functional sequence. In a case where the nucleotide sequence is a non-functional sequence, the purpose of inserting the sequence into the gene that has been cut is to merely disrupt the function of the gene. In a case where the nucleotide sequence is a functional gene (called foreign gene), the purpose of inserting the foreign gene can be, for example, to (i) confirm, by expression of the foreign gene, disruption of the function of the target gene (obtainment of drug tolerance), (ii) visualize an expression pattern of the target gene by an expression of the foreign gene (such as GFP gene), and (iii) express the foreign gene itself.

Insertion of the foreign nucleotide sequence can be inserted by, for example, homologous recombination by use of complementation with a nucleotide sequence in the vicinity of a site of a target gene, after the site has been cut by the CRISPR-Cas system. The homologous recombination can be performed by use of polynucleotide included at both ends of a foreign nucleotide sequence to be inserted while the following regions serve as a flanking sequence: (i) a 5' end side-region that starts from the site of the target gene, which site is to be cut by the CRISPR-Cas system and (ii) a 3' end side-region that starts from the site.

Alternatively, there also exit insertion methods independent of homologous recombination. For example, after a vector having a sequence recognized by gRNA different from gRNA that recognizes a target sequence on a genome is introduced into a cell, target sequences in the cell and in the vector are cut by the CRISPR-Cas system. The vector, which has become single-stranded, is inserted, through a DNA repair function of the cell, into a site on the genome, which site has been cut. Disruption of the function of a target gene by insertion of a foreign nucleotide sequence as in these examples can be called gene editing in genetic engineering.

In the above description, the insertion of a foreign gene into a target gene was described as an example. Note, however, that in view of the gene editing, a site into which a foreign gene is to be inserted can be selected from a region of a genome, which region is not related to gene expression directly or indirectly. If "target gene" is replaced with, for example, "target region on a genome", then a person skilled in the art would immediately understand information on and a method for insertion of a foreign gene into any region on the genome, based on the other descriptions of a target gene herein.

SUMMARY

In summary, the present invention provides the following:
(1) A method for producing a cell in which a target gene is knocked out, the method including the step of: introducing a CRISPR-Cas system into a cell having one or more kinds of target genes, the CRISPR-Cas system being able to produce (i) three or more kinds of guide RNAs for each of the one or more kinds of target genes and (ii) a Cas protein.
(2) The method described in (1), in which the one or more kinds of target genes are knocked out by (i) causing three kinds of guide RNAs to target each of the one or more kinds of target genes and then (ii) causing a Cas protein to cut each of the one or more kinds of target genes.
(3) The method described in (1) or (2), in which the CRISPR-Cas system is a system including (i) three or more kinds of guide RNAs for each of the one or more kinds of target genes and (ii) RNA that encodes a Cas protein.
(4) The method described in any one of (1) through (3), in which the one or more kinds of target genes are two or more kinds of target genes, and the two or more kinds of target genes are knocked out.
(5) The method described in any one of (1) through (4), in which the Cas protein is a Cas9 protein.
(6) The method described in any one of (1) through (5), in which the cell is an animal cell.
(7) The method described in any one of (1) through (6), in which the cell is a fertilized egg.
(8) The method described in any one of (1) through (7), in which the CRISPR-Cas system is introduced into a cytoplasm of the cell.
(9) A method for producing a knockout non-human organism, including the steps of: obtaining an embryo in which a target gene has been knocked out by the method described in any one of (1) through (8); and transplanting the embryo into a pseudopregnant non-human animal, so as to obtain an offspring.
(10) The method described in (9), in which the knockout non-human organism is a knockout non-human animal.
(11) The method described in (9) or (10), in which the target gene is a biallelic gene, and a ratio of whole-body biallelic knockout individuals to all of offspring obtained is 90% or more.
(12) The method described in (11), in which the target gene is two or more kinds of target genes, and a ratio of whole-body biallelic knockout individuals for each of the two or more kinds of target genes to all of offspring obtained is 90% or more.
(13) A knockout non-human organism produced by the method described in any one of (9) through (12).

The present invention will be described in more detail with Examples. However, the present invention is not limited to these Examples.

EXAMPLE

Description of Drawings (FIG. 1)
(A) Schematic diagram of triple-target and single-target CRISPR methods. In the triple-target method, three guide RNAs (gRNA) were designed for each gene (above). The mixture of three gRNAs and Cas9 mRNA were co-injected into the cytoplasm of pronuclear-stage C57BL/6N fertilized eggs. In the single-target method, a single gRNA was injected at a three-fold higher concentration than that in the triple-target method (panel below). In each of the methods, the same amount of total gRNA was used.
(B) Computational simulation that predicts how efficiently one or more alleles are cut out when different numbers of gRNAs are used against the same target gene. The triple-target (red line: above) and single-target (blue line: below) methods were compared. The probabilities of mono-allelic knockout (above), biallelic knockout (i.e. single-gene biallelic knockout, center), and tetra-allelic knockout (i.e. double-gene biallelic knockout, below) were calculated for increasing total gRNA concentrations. The line and shaded area around the line indicate the mean and the standard deviation of 1,000 simulations, respectively. The difference in efficiency between triple-target and single-target strategies became more apparent as the number of target alleles increased. The computational model of the triple-target method estimates minimum efficiency.
(C) Target sequences of the gRNAs for knockout of the Tyrosinase (Tyr) gene. The target sequences of three independent sets of gRNAs were on exon 1 and exons of the Tyr gene. Mouse genomic sequence data were obtained from GRCm38/mm10 via the UCSC Genome Browser (http://genome.ucsc.edu/; (Rhead, B. et al., (2010). The UCSC Genome Browser database: update 2010. Nucleic acids research 38, D613-619)). The short colored bars (blue (left), orange (center), and green (right)) indicate the 20-base target sequences. The target sequences were on the sense strand of the genomic DNA (plus sign refers to the gene's sense strand).
(D) SSA assay for the gRNAs of the Tyr gene. Relative Luciferase activities from the SSA vectors (pSSA-Tyr-1 and pSSA-Tyr-2) were measured. The SSA vector was transfected into 293T cells with empty vector (−), pX330 Cas9 vector without any gRNA (pX330), or pX330 Cas9 and Tyr gRNA (Tyr-1, Tyr-2, or Tyr-3). The relative Luciferase activity for each sample was scaled so that the activity with empty vector (−) was defined as 1. Error bars represent standard deviation (n=3).
(E) Tyr knockout mice produced by the triple-target method. The coat color showed the biallelically knocked out mice.
(F) Comparison of the single- and triple-target CRISPR methods. The table shows the gRNA injection condition and resulting phenotypes (see G of FIG. 2). Embryos: number of injected and transferred embryos; Pups: number of pups born (total); Albino: pups with albino coat color (biallelic knockout); Pigmented: pups with mosaic or wild-type coat color.

(FIG. 2)

(A) Computational simulation that predicts how efficiently one or more alleles are cut out when different numbers of gRNAs are used against the same target gene. Knockout efficiency was calculated for an increasing number of target alleles: single gene mono-allelic (one allele), single gene biallelic (two alleles), double gene biallelic (four alleles), and triple gene biallelic knockout (six alleles). In each simulation, single- (one target per gene), dual- (two targets), triple- (three targets), sextuple- (six targets), and decuple- (ten targets) target methods were compared. In each of the methods, the same amount of total gRNA was used. A computational model of the different methods (except the single-target method) predicts the minimum efficiency.

Figure 2:
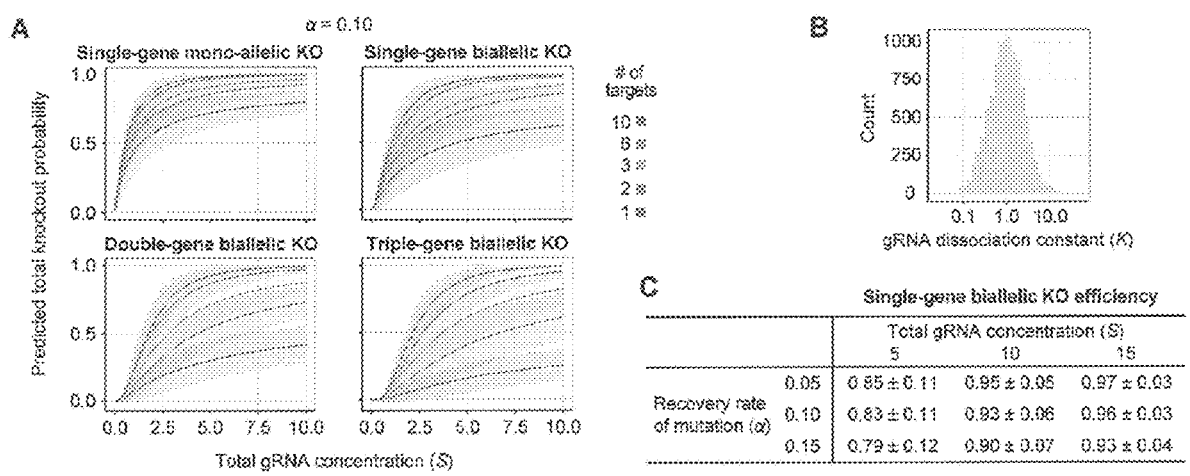
FIG. 2 illustrates a triple-target CRISPR method for highly efficient production of whole-body biallelic knockout mice, in relation to FIG. 1.
Figure 2:
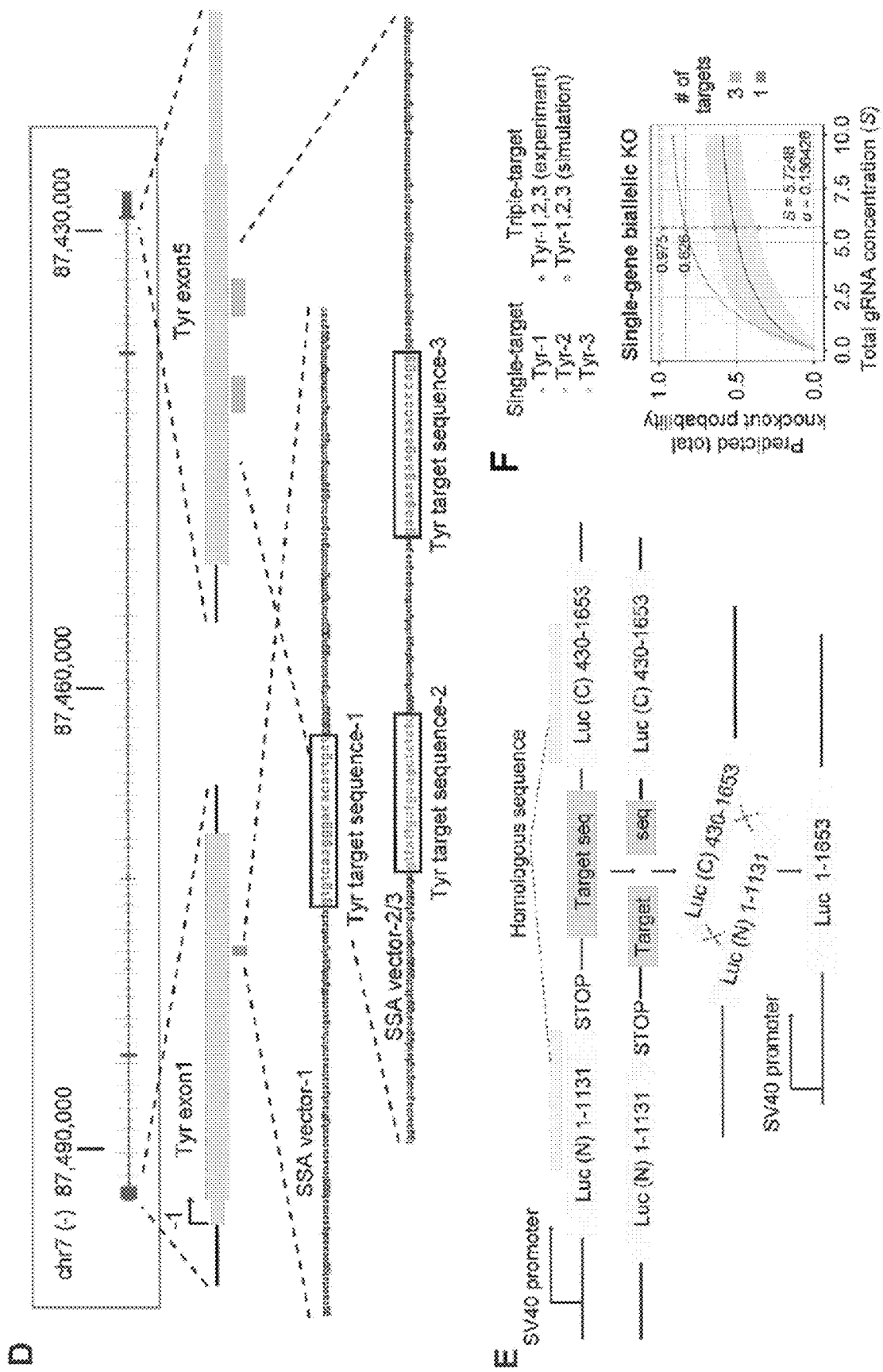
Figure 2:
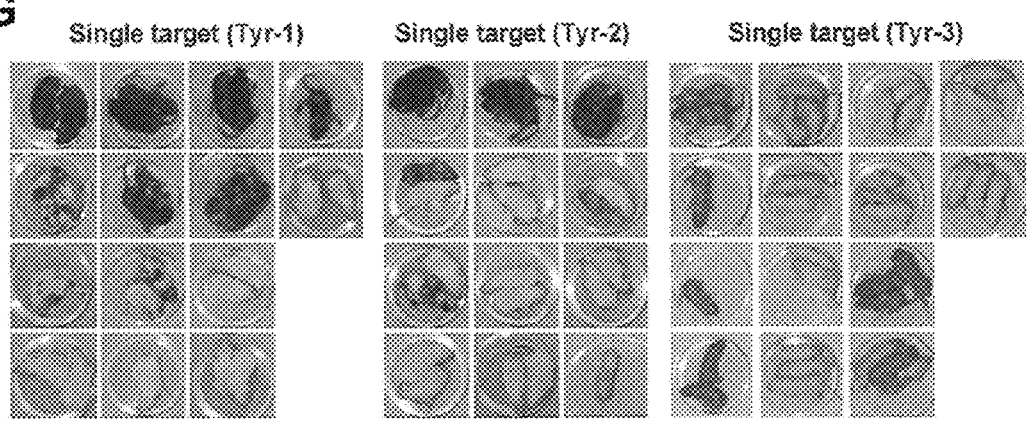
Figure 2:
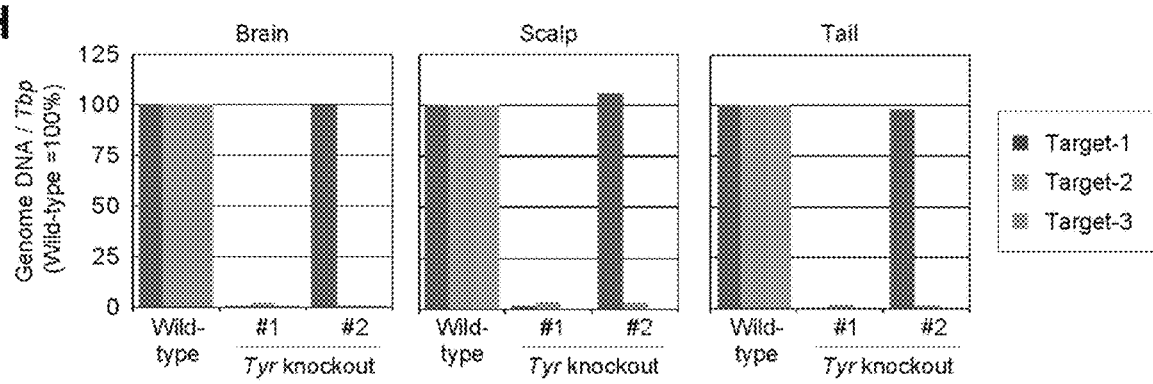

(B) Distribution of the gRNA dissociation constant (K) used in the computational simulation of CRISPR-based knockout (B of FIG. 2). Distribution of the gRNA dissociation constant (K) follows the log-normal distribution with its geometric mean and geometric standard deviation as 1.0 and 2.5, respectively. 1.0 can be used for the geometric mean in the log-normal distribution of the gRNA dissociation constant without loss of generality. Then, three gRNA dissociation constants were estimated from the SSA assay for three gRNAs for Tyr gene ($K_1$=2.32203, $K_2$=1.16562 and $K_3$=0.369466, D of FIG. 1). Since the geometric standard deviation of these values was 2.53097, 2.5 was used for the geometric standard deviation in the log-normal distribution of the gRNA dissociation constant.

(C) Computer simulation that predicts the minimum efficiency (mean±standard deviation) of single-gene biallelic knockout with different recovery rates of mutations ($\alpha$=0.05, 0.10 and 0.15) and total gRNA concentrations (S=5, 10 and 15). Total gRNA concentration (S) is a value relative to the geometric mean of gRNA dissociation constants (1.0).

(D) Sequences of fragment inserted for SSA assay of gRNAs for Tyr gene. The fragment sequences for the SSA vector are shown with three target sequences for Tyr-1, Tyr-2 and Tyr-3 gRNAs, respectively. Mouse genomic sequence data were obtained from GRCm38/mm10 via the UCSC Genome Browser (http://genome.ucsc.edu/; (Rhead, B. et al., (2010). The UCSC Genome Browser database: update 2010. Nucleic acids research 38, D613-619)).

(E) Schematic diagram of single-strand annealing (SSA) assay. The SSA-reporter vector contains 5' and 3' Luciferase gene fragments that shared 702 bp of direct repeats. These fragments were separated by stop codon and gRNA target site. A gRNA/Cas9-mediated double-strand break at the target site induces an SSA reaction between the homologous regions, so as to produce an active Luciferase gene.

(F) Computational simulation with estimated values for a recovery rate of mutation ($\alpha$=0.136) and total gRNA concentration (S=5.72), the computational simulation predicting how efficiently two alleles of a gene are cut out when single or triple gRNAs are used for the same target gene. Three single-target CRISPR models were first constructed with three different dissociation constants ($K_1$=2.32203, $K_2$=1.16562 and $K_3$=0.369466) estimated from the SSA assay results for Tyr-1, Tyr-2, and Tyr-3, respectively. Values of dissociation constants ($K_1$, $K_2$ and $K_3$) are inversely proportional to the DNA-cleavage efficiency in SSA assay, and geometric mean of dissociation constants is set to be 1.0 without loss of generality. The single-target CRISPR efficiencies were Tyr-1 (36.0%), Tyr-2 (54.2%) and Tyr-3 (64.7%), respectively. The single-target CRISPR models and experiments were then compared to estimate the values for a recovery rate of mutation ($\alpha$=0.136) and total gRNA concentration (S=5.72) by least squares method. The triple-target CRISPR efficiencies were experiment (97.5%) and simulation (82.6%).

(G) Coat color of Tyr knockout mice produced with three different single-target gRNAs. See also F of FIG. 1.

(H) The genotyping of Tyr knockout mice. The relative amount of intact DNA for each target sequence was measured by quantitative PCR (qPCR, see D of FIG. 2). The genomic DNA was purified from the brain, scalp and tail of each mouse. The relative amount of intact DNA for each target sequence was scaled so that the level in one wild-type mouse was defined as 100%.

(FIG. 3)

Genome alignments of exome sequence reads. The genomic regions targeted by three gRNAs were shown for wild-type knockout and Tyr knockout #1 and #2. The upper part of each panel shows read coverage, and the lower part shows read alignments (light solid rectangles). Horizontal lines between rectangles indicate read pairing. Different types of mutations (dark solid rectangles) occurring at the target sites are explained in the drawing. The mutations are: inter-exon deletion and inversion; intra-exon deletion and inversion; short deletion; and short insertion.

(FIG. 4)

(A) Pipeline for automatically selecting targets for the triple-target CRISPR method. Candidates were first extracted from exons of a gene, based on these sequences, and were subjected to a series of continuous filtering steps. Candidates were eliminated in cases where (i) the candidates appeared more than once in a mouse genome, (ii) an AT content was less than 45%, (iii) the candidates contained TTTT, or (iv) the candidates were excessively similar to the reverse primer for PCR amplification in construction of gRNA templates. The candidates were also eliminated in cases where the gRNAs had a corresponding secondary structure that was not preferable and where the sequence had a high off-target risk. The candidates which passed these criteria were regarded as suitable targets. These targets are stored in the database.

(B) Distribution of the number of the targets per gene. 81.2% of all the mouse genes had at least three targets. In addition, 71.9% of the genes had more than 6 independent targets. This means that the targets had proper sequences in more than two sets of triple-target CRISPR gRNAs.

(C) Histogram of the number of targets per gene.

(D) Experimental validation of automatically selected targets for Tyr gene. Two sets of additional triple gRNAs (Tyr-4,5,6 for set 2 and Tyr-7,8,9 for set 3) were tested. Photographs show the coat color of the produced mice.

(E) Table shows injection conditions of the gRNAs and resulting phenotype. Embryos: number of injected and transferred embryos; Pups: number of pups born (total); Albino: pups with albino coat color (biallelic knockout); Pigmented: pups with mosaic or wild-type coat color.

(FIG. 5)

(A) Alternative target sequences for Tyr gene. Two sets of alternative target sequences for Tyr were selected from the database of the triple-target CRISPR method (A of FIG. 5). Each of the sets had three targets. Mouse genomic sequence data were obtained from GRCm38/mm10 via the UCSC Genome Browser (http://genome.ucsc.edu/; (Rhead, B. et al., (2010). The UCSC Genome Browser database: update 2010. Nucleic acids research 38, D613-619)). 20-base target sequences are shown.

(B) Web page (http://www.crispr.riken.jp) which contains the database of CRISPR target sequence of triple-target method. Required action can be as little as inputting the names of genes and clicking "Submit". A user can select from the target location of probes and other output options.

(C) Results page on database. The results are shown in a table, and can be downloaded in CSV format (black box).

METHOD (Animal)

C57BL/6NJcl mice were purchased from CLEA Japan Inc., and C57BL/6J mice were purchased from Oriental Yeast Co., Ltd. All mice were given food and water ad libitum. The mice were kept in an environment at an ambient temperature of 21° C. with a relative humidity of 50%. The light was controlled under 12-hour light/12-hour dark cycle. All procedures involving animals and their care were performed according to the RIKEN Regulations for Animal Experiments.

(One-Cell Embryo Microinjection)

C57BL/6N females (4-6 weeks old) were superovulated and mated with C57BL/6N males. Fertilized eggs were collected from the ampulla of the oviduct of plugged C57BL/6N females by micro-dissection, and kept in KSOM medium (Merck Millipore) in a 5% $CO_2$ incubator at 37° C. Cas9 mRNA (100 ng/μl) and gRNAs (150 ng/μl in total) were co-injected into the cytoplasm of fertilized eggs in M2 medium (Merck Millipore) at room temperature. Details of the cytoplasmic injection were described previously (Sumiyama, K., et al., A simple and highly efficient transgenesis method in mice with the Tol2 transposon system and cytoplasmic microinjection. Genomics 95, 306-311). After microinjection, the injected embryos were cultured for 1 hour in KSOM medium (Merck Millipore) in a 5% $CO_2$ incubator at 37° C., and 15-30 embryos were then transferred to the oviducts of pseudopregnant ICR female mice.

(Computational Model to Estimate Minimum Efficiency to Produce Whole-Body Knockout Mice by Multiple-Target CRISPR Methods)

By a computational model described below, the efficiency of different CRISPR methods for producing whole-body knockout mice was estimated. When sufficient Cas9 are provided, efficiency P of single gene mono-allelic knockout can be described as:

$$P = \frac{S}{K+S},\qquad \text{[Math. 1]}$$

where total gRNA concentration and the dissociation constant between the gRNA and its target site are defined as S and K, respectively. This simple phenomenological model is adopted as the first-order approximation of the observed saturation in CRISPR-mediated DNA cutting. The simple phenomenological model describes the net effect, which is therefore intended to mechanistically include the known biochemical processes carried on during DNA cutting (e.g. PAM site binding, as well as, Cas9 remaining bonded to the cut DNA site on both strands following a cut).

When a single allele is targeted by three different gRNAs with dissociation constants ($K_1$, $K_2$, and $K_3$) between each gRNA and its target site, the single-gene mono-allelic knockout efficiency P can be described as:

$$P = 1 - \left(\frac{K_1}{K_1+S/3}\right)\left(\frac{K_2}{K_2+S/3}\right)\left(\frac{K_3}{K_3+S/3}\right) \qquad \text{[Math. 2]}$$

The concentration of each gRNA is S/3 to keep total gRNA concentration as S.

Next, to include the recovery rate (α) at which to recover from single-site damage is introduced as a probability of recovery of a single target site from a damaged state to an intact state. When α is considered, the single-gene mono-allelic knockout efficiency P for a single-target method (A and B of FIG. 1 and A of FIG. 2) can be described as:

$$P = \frac{S(1-\alpha)}{K+S} \qquad \text{[Math. 3]}$$

Similarly, the single-gene mono-allelic knockout efficiency P for a triple-target method (A and B of FIG. 1 and A of FIG. 2) can be described as:

$$P = \frac{S(K_1 K_2 + K_2 K_3 + K_3 K_1)(1-\alpha) + S^2(K_1+K_2+K_3)(1-\alpha^2) + S^3(1-\alpha^3)}{(K_1+S/3)(K_2+S/3)(K_3+S/3)} \qquad \text{[Math. 4]}$$

When a single allele is targeted by N different sites, the dissociation constant between each gRNA and its target site is defined as $K_i$ (i=1 ... N). The single-gene mono-allelic knockout efficiency P for a N-tuple-target method (A of FIG. 2) can be then described as:

$$P = \frac{S(K_1 \ldots K_{N-1} + \ldots + K_2 \ldots K_N)(1-\alpha) + \ldots + S^{N-1}(K_1 + \ldots + K_N)(1-\alpha^{N-1}) + S^N(1-\alpha^N)}{\prod_{i=1}^{N}(K_i+S)} \qquad \text{[Math. 5]}$$

The single-gene mono-allelic knockout efficiency P was calculated 1,000 times for each given α, N, and S. Every time calculation was performed, one set of K (1, 3, and N for single-, triple-, and N-tuple-target methods, respectively) were picked randomly from a log-normal distribution whose geometric mean and geometric standard deviation were 1.0 and 2.5, respectively (B of FIG. 2). 1.0 can be used for the geometric mean of the distribution of the dissociation constant K without loss of generality. In order to estimate its geometric standard deviation, three kinds of gRNA dissociation constants were first estimated from the SSA assay for three gRNAs for Tyr gene ($K_1$=2.32203, $K_2$=1.16562 and $K_3$=0.369466 for Tyr-1, Tyr-2 and Tyr-3, respectively, D of FIG. 1). K is estimated as a value inversely proportional to the DNA-cleavage efficiency measured from SSA assays. Since the geometric standard deviation of these estimated K values was 2.53097, 2.5 was used for the geometric standard deviation. In order to estimate the efficiency of single-gene biallelic knockout, double-gene biallelic knockout, and triple-gene biallelic knockout, $P^2$, $P^4$ and $P^6$, respectively, were calculated (B of FIG. 1 and A of FIG. 2). In the examples shown in B of FIG. 1 and A of FIG. 2, α=0.10. Since there is uncertainty for α and S in vivo, single-gene biallelic knockout efficiency $P^2$ was also calculated with different values of α and S (C of FIG. 2, α=0.05, 0.10, 0.15, and S=5, 10, 15, respectively). Calculated knockout efficiencies for multiple-target methods (N>1) predict the "minimum" efficiency of knockout since the probability of other type of mutations was not included in the multiple-target CRISPR models (e.g. large deletions induced by multiple-target CRISPR methods), which is difficult for a DNA repair system to recover back to the intact state.

To estimate realistic values for α and S, three single-target CRISPR models were constructed with different dissociation constants ($K_1$=2.32203, $K_2$=1.16562 and $K_3$=0.369466) estimated from the SSA assay results for Tyr-1, Tyr-2, and Tyr-3, respectively. These models were compared with the experimental results of single-target CRISPR (36.0%, 54.2%, and 64.7% for Tyr-1, Tyr-2 and Tyr-3, respectively), and a least squares method was used to estimate the realistic values for a recovery rate of mutation (α=0.136428) and total gRNA concentration (S=5.7248), respectively. Then, 1,000 simulations were performed to calculate a single-gene biallelic knockout efficiency ($P^2$) for single-target (N=1) and triple-target (N=3) CRISPR models with α=0.136 and K which was randomly picked from the log-normal distribution in B of FIG. 2. As a result, a single-gene biallelic knockout efficiency ($P^2$) for single-target (N=1) and triple-target (N=3) CRISPR models at S=5.7248 were 0.512±0.138 and 0.826±0.098 (mean±standard deviation), respectively (G of FIG. 2). This indicates that a triple-target CRISPR method is much more efficient than a single-target CRISPR method in a case where the realistic parameter values were used for α and S. In addition, the triple-target method using the mixture of Cas9 mRNA and three kinds of gRNAs achieved almost perfect efficiency (97.5%, E and F of FIG. 1). The efficiency of the triple-target method is much more efficient than the predicted minimum efficiency (82.5%) (G of FIG. 2).

(Design of Target Sequences for gRNA)

Target sequences for Tyr (C of FIG. 1) were designed by use of Jack Lin's online CRISPR gRNA finder (http://spot.colorado.edu/~slin/cas9.html). Possible off-target sequences within the mouse genome for each target sequence were checked by use of the CRISPR Design Tool (http://tools.genome-engineering.org) (Non-Patent Literature 9).

Figure 4:
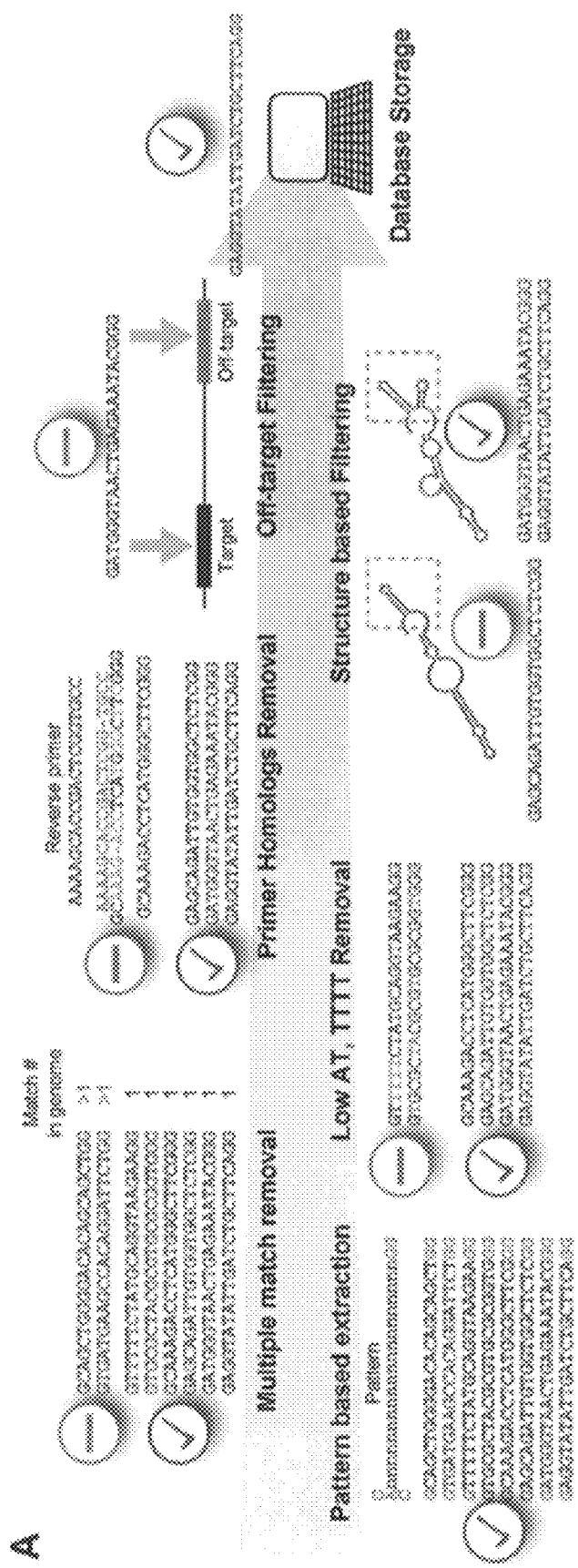
FIG. 4 shows the publicly available database for a triple-target CRISPR method.
Figure 4:
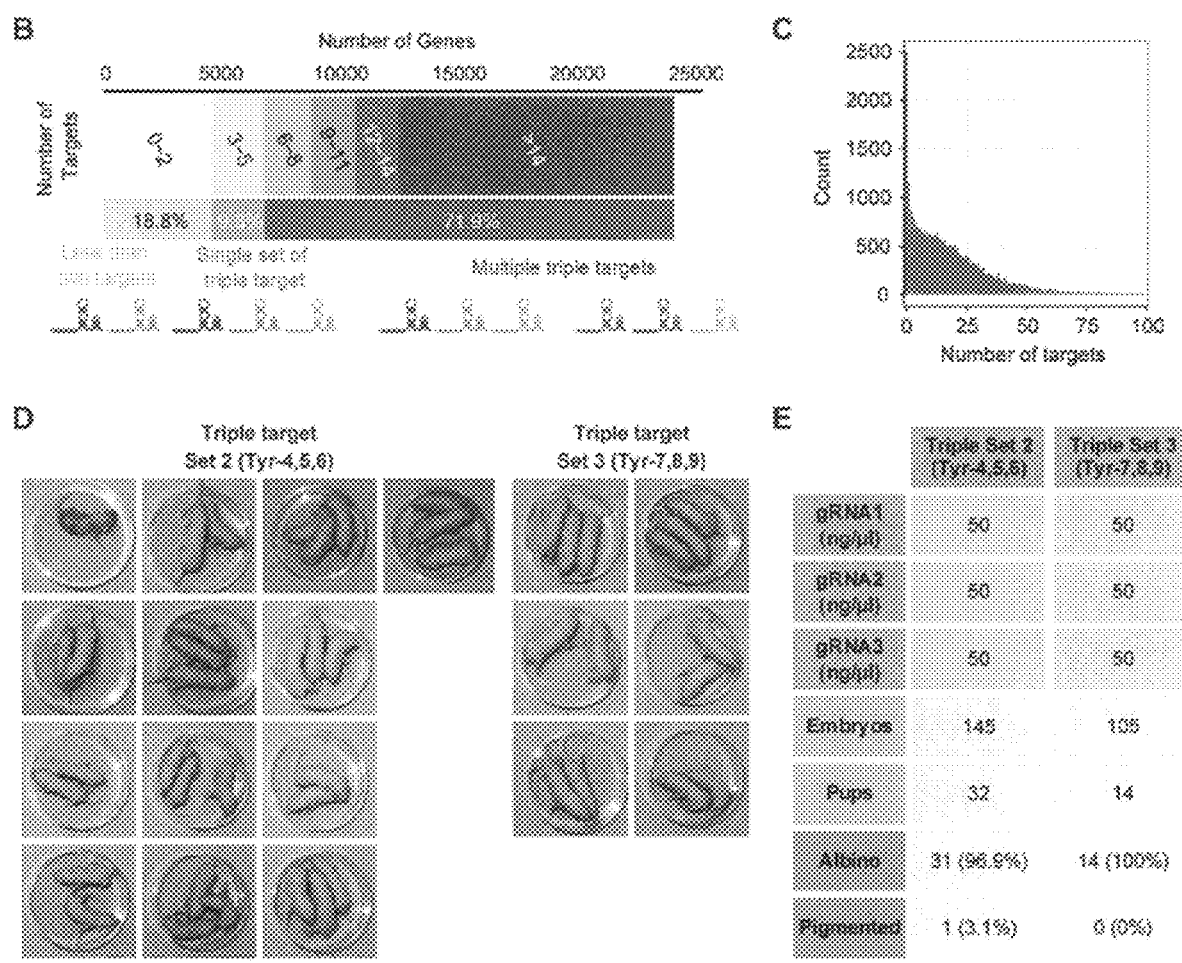
Figure 5A:
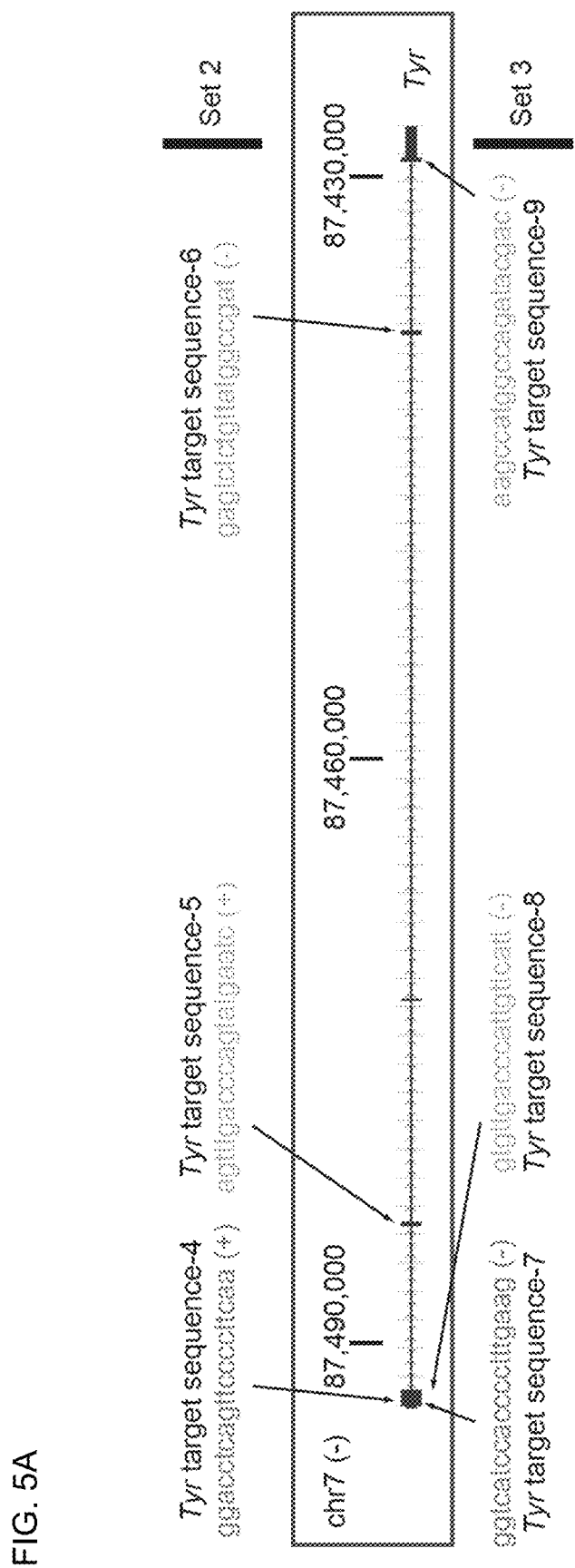
FIG. 5 shows the publicly available database for a triple-target CRISPR method, in relation to FIG. 4.
Figure 5B:
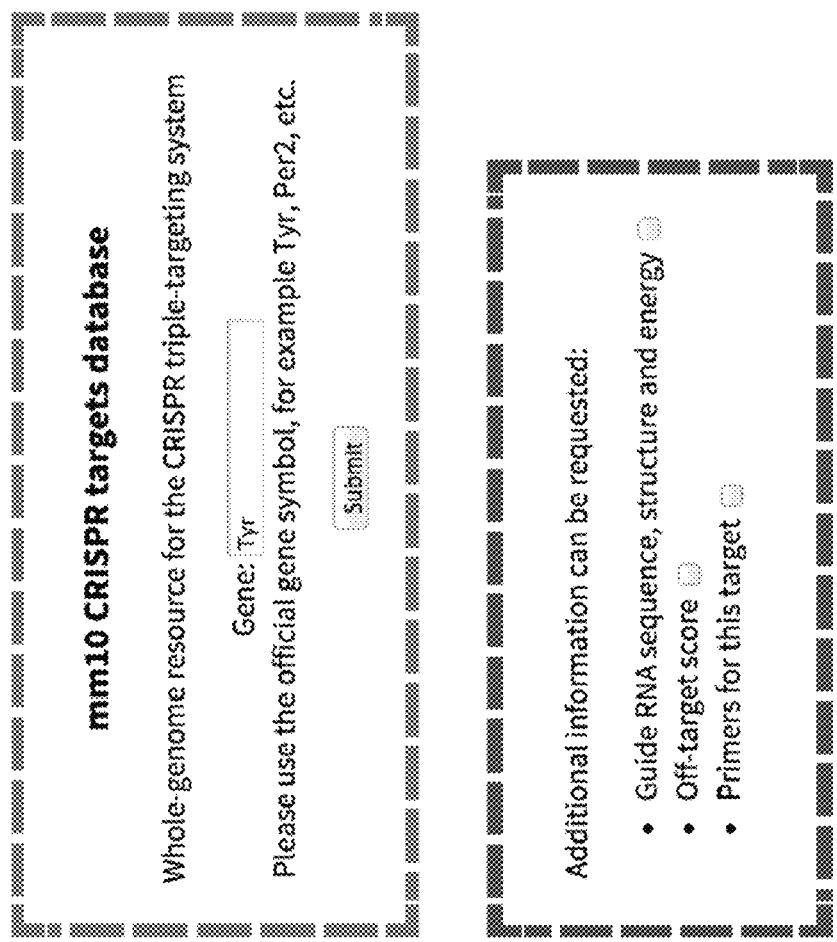
Figure 5B:
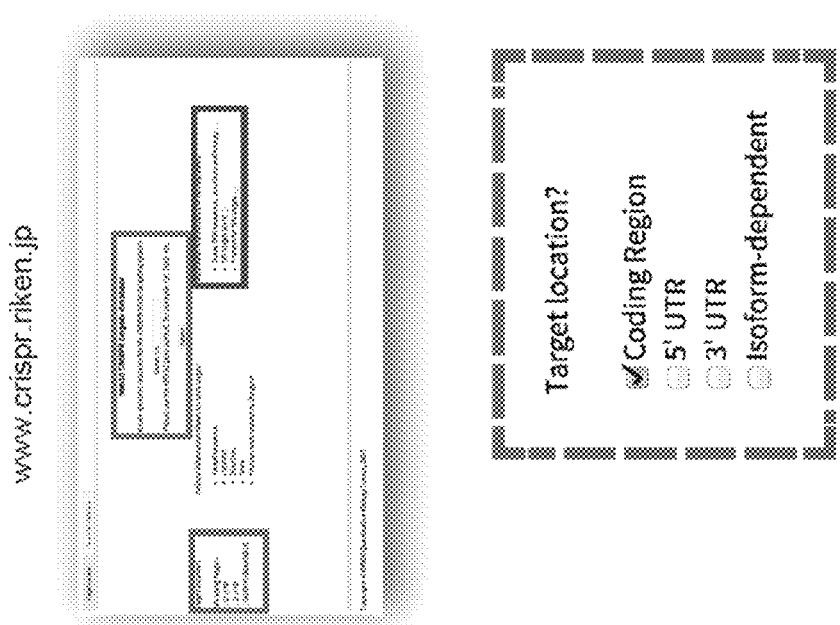
Figure 5C:
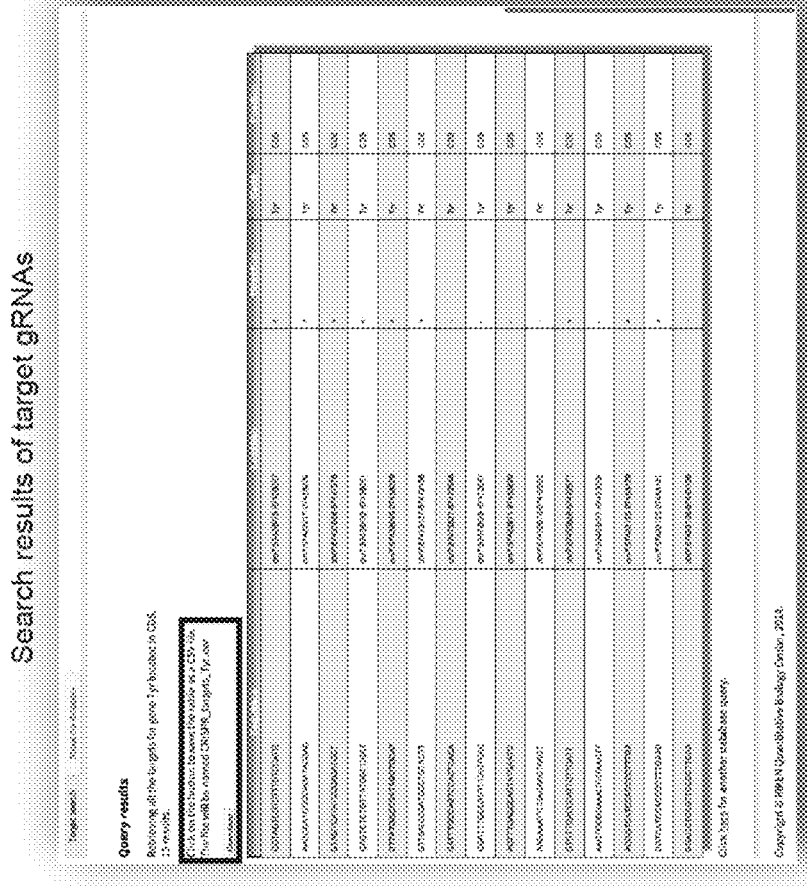

Alternative target sequences for Tyr (A of FIG. 5) were selected from the list resulting from the mm10 CRISPR/Cas9 database (A of FIG. 4, http://www.crispr.rikenjp/).

(Construction of pGL3-SSA Plasmid for Single-Strand Annealing (SSA) Assay)

Two partial fragments of the pGL3-control vector (Promega), which contained the 5'- or 3'-partial sequence of the Luciferase gene, were amplified by use of PCR with the following primers:

(SEQ ID NO. 1)
1) forward 5'-GTAAAATCGATAAGGATCCGTCGAC-3'

(Hokkaido System Science), and (SEQ ID NO. 2)
2) reverse: 5'-CAGCTGAAACTGCAGAAAGATATCAAAGAATTCTT AATCCAGATCCACAACCT TGCTTC-3', 1) and 2) being used as primers amplifying part of the vector backbone and the 5' portion of the Luciferase gene, and (SEQ ID NO. 3)
3) forward 5'-GATATCTTTCTGCAGTTTCAGCTGCCAATCATCCAA AAAATTATTATCATGG-3', and (SEQ ID NO. 4)
4) reverse 5'-CATCGGTCGACGGATCCTTATCG-3', 3) and 4) being used as primers amplifying part of the vector backbone and the 3' portion of the Luciferase gene. Both PCR products were digested by PstI and BamHI, and mutually ligated. The resulting vector, which contained multiple cloning sequences (5'-TAAGAATTCTTTGA-TATCTTTCTGCAGTTTCAGCTG-3' (SEQ ID NO. 5): Stop-EcoRI-EcoRV-PstI-PvuII) between the 5'- and 3'-partial Luciferase sequences, was designated as pGL3-SSA.

(Construction of pSSA-Tyr-1 and pSSA-Tyr-2/3 Plasmids)

199-base and 200-base fragments containing the target sequences for Tyrosinase (Tyr-1, and both Tyr-2 and Tyr-3, respectively) were amplified from C57BL/6 mouse genomic DNA by use of PCR. The PCR products were 5'-end phosphorylated with the Mighty Cloning kit (TaKaRa), and inserted into the EcoRV sites of the pGL3-SSA plasmid (see above). The resulting vectors were designated as pSSA-Tyr-1 and pSSA-Tyr-2/3, respectively.

```
Oligonucleotide Sequences for target sequences
(Hokkaido System Science)
pSSA-Tyr-1:
Forward oligonucleotide:
                                    (SEQ ID NO. 6)
5'-GGCACCTATGGCCAAATGAACAATGGG-3'

Reverse oligonucleotide:
                                    (SEQ ID NO. 7)
5'-GTTCCCACAATAACAAGAAAAGTCTGTGCC-3' pSSA-Tyr-2/3:
Forward oligonucleotide:
                                    (SEQ ID NO. 8)
5'-TGGAACAAGCCAGTCGTATCTGGCC-3'

Reverse oligonucleotide:
                                    (SEQ ID NO. 9)
5'-TCACAGATGGCTCTGATACAGCAAGCTG-3'
```

(Construction of pX330-Tyr-1, pX330-Tyr-2, and pX330-Tyr-3 Plasmids)

Oligonucleotides (Hokkaido System Science) containing target sequences for Tyrosinase (Tyr-1, Tyr-2, and Tyr-3, respectively) were annealed and inserted into the BbsI sites downstream of the U6 promoter on the pX330 plasmid [Addgene, #42230, (Cong et al., (2013). Multiplex genome engineering using CRISPR/Cas systems. Science 339, 819-823; Non-Patent Literature 9]. The resulting vectors were designated as pX330-Tyr-1, pX330-Tyr-2, and pX330-Tyr-3, respectively.

```
Oligonucleotide sequences for target sequences
Tyr-1:
Forward oligonucleotide:
                                    (SEQ ID NO. 10)
5'-CACCGTGTCAAGGGACACACTGCT-3'

Reverse oligonucleotide:
                                    (SEQ ID NO. 11)
5'-AAACAGCAGTGTGTCCCTTGACAC-3'

Tyr-2:
Forward oligonucleotide:
                                    (SEQ ID NO. 12)
5'-CACCGTTATTGCTGCAGCTCTCTC-3'

Reverse oligonucleotide:
                                    (SEQ ID NO. 13)
5'-AAACGAGAGAGCTGCAGCAATAAC-3'

Tyr-3:
Forward oligonucleotide:
```

```
5'-CACCGAAGAAGAAGCAACCCCAGG-3'        (SEQ ID NO. 14)

Reverse oligonucleotide:
                                      (SEQ ID NO. 15)
5'-AAACCCTGGGGTTGCTTCTTCTTC-3'
```

(SSA Assay)

293T cells were maintained in DMEM (Life Technologies) supplemented with 10% FBS (JRH Biosciences) and antibiotics (100 U/ml penicillin and 100 µg/ml streptomycin; Life Technologies). One day prior to transfection, the cells were plated onto six-well plates at a density of 4×10$^5$ cells per well. On the following day, the cells were co-transfected by use of FuGene6 (Roche) with 1 µg of pSSA-Tyr-1 or pSSA-Tyr-2/3 reporter plasmids in the presence of the following constructs, as indicated in D of FIG. 1: 0 or 2 µg of pX330, pX330-Tyr-1, pX330-Tyr-2, or pX330-Tyr-3 plasmid, according to the manufacturer's instructions. An empty vector was used to bring the total amount of DNA to 3 µg per well. In addition, 50 ng of a phRL-CMV plasmid [Renilla luciferase (RLuc) reporter vector, Promega] was included in each transfection as an internal control for transfection efficiency. 48 hours after transfection, the cells were harvested and assayed with use of the Dual-Luciferase Reporter Assay System (Promega). The Luciferase activity was normalized to the Rluc activity.

(Cas9 mRNA Synthesis)

p3s-Cas9HC [Addgene, #43945, (Cho, S. W., et al., (2013). Targeted genome engineering in human cells with the Cas9 RNA-guided endonuclease. Nature biotechnology 31, 230-232], which includes a T7 promoter-fused Cas9 coding region, was digested with XbaI (TaKaRa), and used as the template for in vitro transcription with use of the mMESSAGE mMACHINE T7 kit (Life Technologies). The Cas9 mRNA was purified with use of the MEGAclear kit (Life Technologies).

(gRNA Synthesis)

The gRNA templates for Tyr (D of FIG. 1) were fused to the T7 promoter and amplified from the pX330-Tyr by PCR with use of the primers listed below (Hokkaido System Science) (Non-Patent Literature 4).

The gRNA templates for Tyr were directly synthesized and fused to the T7 promoter by PCR. First, the partial fragments of the gRNA templates including each target sequence were amplified from pX330 plasmids (Addgene, #42230) by use of PCR with the Common Reverse primer and the Common Reverse primer and Forward primer-1 (Hokkaido System Science) for each target sequence. Subsequently, the T7 promoter-fused gRNA templates were amplified from the diluted PCR products by use of PCR with the Common Reverse primer and Forward primer-2 (Hokkaido System Science) for each target sequence.

```
Oligonucleotide sequences for T7g-RNA templates
Tyr (set-2)
gRNANo.4
1
                                      (SEQ ID NO. 16)
CACTATAGGGACCTCAGTTCCCCTTCAAGTTTTAGAGCTAGAA

ATAGC 2
                                      (SEQ ID NO. 17)
GGGCCTAATACGACTCACTATAGGGACCTCAGTTCCCCTTCAA

G gRNANo.5
1
                                      (SEQ ID NO. 18)
CACTATAGGGTTTGACCCAGTATGAATCGTTTTAGAGCTAGAA

ATAGC 2
                                      (SEQ ID NO. 19)
GGGCCTAATACGACTCACTATAGGGTTTGACCCAGTATGAATC

G gRNANo.6
1
                                      (SEQ ID NO. 20)
CACTATAGGAGTCTCTGTTATGGCCGATGTTTTAGAGCTAGAA

ATAGC 2
                                      (SEQ ID NO. 21)
GGGCCTAATACGACTCACTATAGGAGTCTCTGTTATGGCCGAT

G.

Tyr (set-3)
gRNANo.7
1
                                      (SEQ ID NO. 22)
CACTATAGGGTCATCCACCCCTTTGAAGGTTTTAGAGCTAGAA

ATAGC 2
                                      (SEQ ID NO. 23)
GGGCCTAATACGACTCACTATAGGGTCATCCACCCCTTTGAAG

G gRNANo.8
1
                                      (SEQ ID NO. 24)
CACTATAGGTGTTGACCCATTGTTCATTGTTTTAGAGCTAGAAA

TAGC 2
                                      (SEQ ID NO. 25)
GGGCCTAATACGACTCACTATAGGTGTTGACCCATTGTTCATT

G gRNANo.9
1
                                      (SEQ ID NO. 26)
CACTATAGGAGCCATGGCCAGATACGACGTTTTAGAGCTAGAA

ATAGC 2
                                      (SEQ ID NO. 27)
GGGCCTAATACGACTCACTATAGGAGCCATGGCCAGATACGA

CG
```

The T7 promoter-fused gRNA PCR fragments were used as the template for in vitro transcription using the MEGAshortscript T7 kit (Life Technologies). The gRNAs were purified with use of the MEGAclear kit (Life Technologies).

```
Common reverse oligonucleotide for T7-gRNAs:
                                      (SEQ ID NO. 28)
5'-AAAAGCACCGACTCGGTGCC-3'  (Non-Patent Literature 4)

Oligonucleotide sequences for T7-gRNAs of Tyr (set
```

-continued

1)
Tyr-1 Forward oligonucleotide:
(SEQ ID NO. 29)
5'-GGGCCTAATACGACTCACTATAGGTGTCAAGGGACACACTGCT-3'

Tyr-2 Forward oligonucleotide:
(SEQ ID NO. 30)
5'-GGGCCTAATACGACTCACTATAGGTTATTGCTGCAGCTCTCTC-3'

Tyr-3 Forward oligonucleotide:
(SEQ ID NO. 31)
5'-GGGCCTAATACGACTCACTATAGGAAGAAGAAGCAACCCCAGG-3'

Oligonucleotide sequences of triple-target gRNAs (T7-gR-NAs) for Tyr (sets 2 and 3) genes are as described above.

(Genotyping of Tyr Knockout Mice by Quantitative PCR (qPCR) and Sequencing)

First, the genomic DNA of wild type and Tyr knockout mice were prepared from their brains, scalps, and tails with use of the Wizard Genomic DNA Purification Kit (Promega) according to the manufacturer's instructions. Then, qPCR analysis for genotyping of these mice was performed with use of the ABI PRISM 7900 (Applied Biosystems)/QuantStudio7 Real-Time PCR System (Life Technologies), SYBR Premix Ex Taq GC (TaKaRa) and primers for qPCR (Hokkaido System Science), and it was confirmed that the quantitative qPCR results matched with each other among the genomic DNAs extracted from brains, scalps and tails. The absolute target site abundance was calculated by use of a standard curve obtained from wild-type genomic DNA. The amount of Tbp (Tsujino et al., (2013) Establishment of TSH beta real-time monitoring system in mammalian photoperiodism. Genes to cells: devoted to molecular & cellular mechanisms 18, 575-588) was quantified and used as an internal control.

```
Primer sequence (Hokkaido System Science) used
for quantitative PCR
Tyr-1:
                                    (SEQ ID NO. 32)
Forward primer: 5'-GTGTCAAGGGACACACTGCTTGG-3'

(SEQ ID NO. 33)
Reverse primer: 5'-CTGTGCCAAGGCAGAAACCCTGG-3'

Tyr-2:
                                    (SEQ ID NO. 34)
Forward primer: 5'-GTTATTGCTGCAGCTCTCTCTGG-3'

(SEQ ID NO. 35)
Reverse primer: 5'-GTCTTTGTCCATGAGGAGTGGCTG-3'

Tyr-3:
                                    (SEQ ID NO. 36)
Forward primer: 5'-GTTATTGCTGCAGCTCTCTCTGG-3'

(SEQ ID NO. 37)
Reverse primer: 5'-TCACAGATGGCTCTGATACAGCAAG-3'

Tbp:
                                    (SEQ ID NO. 38)
Forward primer: 5'-CCCCCTCTGCACTGAAATCA-3'

(SEQ ID NO. 39)
Reverse primer: 5'-GTAGCAGCACAGAGCAAGCAA-3'
```

(Protein Quantification)

An absolute amount of TYR protein was quantified by selected reaction monitoring (SRM) MS. Sample processing for the MS analysis was performed according to a phase-transfer surfactant (PTS) protocol (Masuda, T., Tomita, M., and Ishihama, Y. (2008). Phase transfer surfactant-aided trypsin digestion for membrane proteome analysis. J Proteome Res 7, 731-740) with several modifications. To analyze TYR abundance, ears obtained from the mutant mice Tyr #3 and Tyr #4 were used. In brief, the tissues were homogenized by sonication in PTS buffer (12 mM sodium deoxycholate, 12 mM sodium N-lauroylsarcosinate, and 50 mM $NH_4HCO_3$) containing a phosphatase inhibitor cocktail (Nacalai Tesque) and a protease inhibitor cocktail (Nacalai Tesque) and were clarified by centrifugation at 10,000×g for 10 minutes. The resulting homogenates were frozen in liquid nitrogen and stored at −80° C. until use. Protein concentrations were determined by Quick Start Bradford Dye Reagent (Bio-Rad).

As internal standards, the synthetic peptides with the isotope labeled lysine residue and isotope labeled arginine residue ($^{13}C_6$-Lys and $^{13}C_6^{15}N_4$-Arg, respectively) were added. The synthetic peptides were pre-quantified and digested to produce specific sequences (DTLLGGSEIWR for the quantification of Tyr protein) for the quantification of target proteins according to our newly developed method described elsewhere. The mixtures of proteins and internal standards were subjected to cysteine reduction and alkylation (10 mM TCEP at 37° C. for 1 hour and 15 mM iodoacetamide at 37° C. for 30 minutes in dark) followed by 5-fold dilution with 50 mM $NH_4HCO_3$ solution. Then, enzymatic cleavage of proteins was performed by 8 hour-incubation with use of 1:50 (w/w) LysC followed by 16 hour-incubation with use of 1:50 (w/w) trypsin at 37° C. The digestion (the enzymatic cleavage of the proteins) was stopped by mixing an equal volume of ethyl acetate in the presence of 0.5% TFA. The surfactants in the sample were removed by discarding the ethyl acetate phase. The remaining aqueous phase containing peptides was dried with use of SpeedVac (Thermo Scientific). The dried peptide mixture was then dissolved in an analytical buffer (2% acetonitrile and 0.1% TFA). The resulting peptide solution was desalted with use of StageTip (Rappsilber, J., Mann, M., and Ishihama, Y. (2007). Protocol for micro-purification, enrichment, pre-fractionation and storage of peptides for proteomics using StageTips. Nature protocols 2, 1896-1906). 100 μg of the peptide mixture prepared from ear was pre-fractionated into 6 fractions by StageTip-based fractionation (Wisniewski, J. R., Zougman, A., and Mann, M. (2009). Combination of FASP and StageTip-based fractionation allows in-depth analysis of the hippocampal membrane proteome. J Proteome Res 8, 5674-5678), and then the fractions were dissolved in 14-30 of analytical buffer.

The resulting peptide mixture corresponding to approximately 1 μg of proteins was analyzed by liquid chromatography (LC)-MS using a triple quadruple mass spectrometer (TSQ Vantage EMR mass spectrometer, Thermo Scientific). The LC-MS is equipped with a captive spray ionization source (Michrom Bioresources), a nano-Advance UHPLC system (Bruker Daltonics), and an HTC-PAL autosampler (CTC Analytics) with a trap column (0.3×5 mm, L-column, ODS, Chemicals Evaluation and Research Institute, Japan). Analytical samples were separated by reversed phase chromatography which was performed such at a concentration gradient of acetonitrile from 4% to 36% in 0.5% acetic acid over 105 minutes at a flow rate 300 nL/min. with use of a home-made capillary column (length of 200 mm and inner diameter of 100 μm) packed with 2 μm C18 resin (L-column2, Chemicals Evaluation and Research Institute, Japan). The resulting eluted substance was directly electrosprayed (1.6 kV) into the MS.

To analyze TYR protein in ear samples, the heavy version and light version of DTLLGGSEIWR were monitored by LC-SRM-MS by use of the SRM transitions of m/z 623.8 to 804.4 (for the light version) and m/z 628.8 to 814.4 (for the heavy version).

(Library Preparation for Exome Sequencing)

Exome libraries were constructed with use of SureSelectQXT Reagent Kit (Cat. No. G9681A, Agilent Technologies) and SureSelectXT Mouse All Exon Kit V1 (Cat. No. 5190-4641, Agilent Technologies) according to the manufacturer's instructions. Fragmentation and adapter-tagging of purified genomic DNA samples were performed by transposase-based reaction. After an amplification of adapter-tagged DNA library, purification was performed with use of AMPure XP beads (Beckman Coulter). The purified libraries were hybridized to the SureSelect capture library, and hybridized DNA was collected with use of streptavidin-coated beads. The enriched DNA libraries were amplified by use of PCR using the appropriate pair of dual indexing primers to add index tags for the Illumina TruSeq system. In each purification step, the length distribution and concentration of DNA molecules in libraries were analyzed with use of the 2100 Bioanalyzer (Agilent Technologies).

(Exome Sequencing and Indel Detection)

The libraries were subjected to on-board cluster generation with use of TruSeq Rapid PE Cluster Kit (Cat. No. PE-402-4001) and sequenced on Rapid Run Mode of Illumina HiSeq 1500 (Illumina) to obtain paired-end reads with 126 cycles was obtained with use of three 50-cycle SBS kits (Cat. No. FC-402-4002). It should be noted that surplus reagents were used as demonstrated previously (Tatsumi K, N. O., Itomi K, Tanegashima C, Kuraku S (2015, in press.). Optimization and cost-saving in tagmentation-based mate-pair library preparation and sequencing. Biotechniques)). 5% PhiX spike-in was added to each lane as control. Image analysis and base calling were executed with use of the standard Illumina software consisting of HiSeq Control Software (HCS) ver. 2.0.12.0 and Real-Time Analysis (RTA) ver. 1.17.21.3. Quality of the raw sequence data were controlled by FastQC ver. 0.11.1 (http://www.bioinformatics.bbsrc.ac.uk/projects/fastqc/). Removal of adapter sequences and low-quality reads was performed with use of Trim Galore ver. 0.3.3 with the parameters "-e 0.1 -q 30" (http://www.bioinformatics.babraham.ac.uk/projects/trim_galore/). Additionally, reads with the average per-base quality score of not more than 30 were removed from an original script. The reads filtered as described above were aligned with the genome sequences GRCm38/mm10 by BWA ver. 0.7.10-r789 using the BWA-MEM algorithm (Li and Durbin, 2010). Potential PCR duplicates among the mapped paired reads were removed with use of the MarkDuplicates function of Picard Tools ver. 1.122 (http://picard.sourceforge.net/). The sequencing statistics including the number of reads, mapping rate, and exome on-bait coverages were summarized by the CalculateHsMetrics function of Picard Tools.

Local realignment of the mapped reads was performed by RealignerTargetCreator and IndelRealigner of the Genome Analysis Toolkit (GATK) package ver. 3.2-2 (McKenna, A., Hanna, M., Banks, E., Sivachenko, A., Cibulskis, K., Kernytsky, A., Garimella, K., Altshuler, D., Gabriel, S., Daly, M., et al. (2010). The Genome Analysis 41 Toolkit: a MapReduce framework for analyzing next-generation DNA sequencing data. Genome research 20, 1297-1303), and recalibration based on per-base quality score were performed with use of the BaseRecalibrator and PrintReads functions. For these processes, the mm9-based exome region data with 100 bp padding provided by Agilent Technologies was converted to mm10 with use of the UCSC LiftOver program (https://genome.ucsc.edu/util.html) (Rhead, B et al., (2010). The UCSC Genome Browser database: update 2010. Nucleic acids research 38, D613-619), and insertion and deletion mutations (indels) obtained from NCBI dbSNP (build 137) were used as known sites. The sample-specific indels were called with use of the HaplotypeCaller in GATK after applying local realignment and recalibration performed as described above.

SnpEff package ver. 4.0E (Cingolani, P., Platts, A., Wang le, L., Coon, M., Nguyen, T., Wang, L., Land, S. J., Lu, X., and Ruden, D. M. (2012). A program for annotating and predicting the effects of single nucleotide polymorphisms, SnpEff: SNPs in the genome of *Drosophila melanogaster* strain w1118; iso-2; iso-3. Fly 6, 80-92) was used to filter and annotate the indels that causes high-impact coding variants. The following 1 and 2) were defined as high-impact mutations: 1) the indels categorized in "HIGH" by the SnpEff definition; and 2) the in-frame indels. The indels in both the samples and the control were removed, in comparison with the indels in the control. On- and off-target indels were visualized and evaluated on the UCSC Integrative Genomics Viewer (IGV) ver. 2.3.36 (Thorvaldsdottir, H., Robinson, J. T., and Mesirov, J. P. (2013). Integrative Genomics Viewer (IGV): high-performance genomics data visualization and exploration. Briefings in bioinformatics 14, 178-192.). The exome sequencing data have been deposited and are available in the DNA Data Bank of Japan (DDBJ). The accession numbers for Tyr knockout data are DRA003478.

(CRISPR gRNA Database Development)

The first step in automatically detecting gRNA sites is to extract candidate targets. Although the process is described here for a single gene, the process to be repeated for all genes in a case where the method is carried out. With use of the genome annotation file and the genome sequence, the sequences of all exons shared by all known isoforms of the gene were extracted. This was necessary to ensure that a gene, rather than only a few of its isoforms, was to be targeted. Then, all the sequences that matched the [G, C, or A]$N_{20}$GG pattern and those for which the complement matched this pattern were extracted. This list represents all the possible candidates for the gene. The next steps were used to filter this list and to keep only suitable targets. Each target needed to pass all the steps, so that the order did not have any impact on the selection. These steps were therefore performed in the most computationally efficient order.

The candidate gRNAs need to target a unique site. With use of Bowtie2 (Langmead, B., and Salzberg, S. L. (2012). Fast gapped-read alignment with Bowtie 2. Nature methods 9, 357-359), all the candidates that had multiple exact matches in the genome (irrespective of location) were eliminated. Targets with a low AT percentage (below 45%), which have a risk of binding strongly to off-target sites, were also removed, and targets that contained TTTT, which tend to break the gRNA's secondary structure, were also removed. Because the targets appeared in the forward primer during synthesis, it is necessary to make sure that targets were not excessively similar to the reverse primer (see above "Common reverse oligonucleotide for T7-gRNAs"). This was achieved by use of the Needleman-Wunsch algorithm (Needleman, S. B., and Wunsch, C. D. (1970). A general method applicable to the search for similarities in the amino acid sequence of two proteins. Journal of molecular biology 48, 443-453). Then, the Vienna RNA-fold package (Lorenz, R. et al., (2011). ViennaRNA Package 2.0. Algorithms for molecular biology: AMB 6, 26) was used to compute the gRNA's secondary structure. All candidates for which the stem loop structure for Cas9 recognition could not fold (Nishimasu, H., et al., (2014). Crystal structure of Cas9 in complex with guide RNA and target DNA. Cell 156, 935-949) were eliminated, except in cases where the folding energy was above −18 (which indicates that the 'wrong' structure was very unstable). Finally, the off-target risk was evaluated by implementation of the Zhang tool (Non-Patent Literature 9). To ensure that all targets stored in the database were as safe as possible, candidates with a score below 75 were rejected.

Candidates that passed all the filtering steps were saved and stored in the database. The data is accessible online at http://crispr.riken.jp. (The data is password-protected while the research paper is under review. The data can be viewed with the login name "DB" and the password "UnderReview".)

(Statistical Significance Test)

Statistical significance was evaluated by Dunnett's test or Welch's two-sample t-test, and represented as follows: *p<0.05, p<0.01, and *p<0.001. Those which were evaluated as insignificant were represented as n.s. Analyses were performed with use of Microsoft Excel or R version 3.1.0.

<Results>

(Triple-Target CRISPR Achieves Almost Perfect Knockout Efficiency.)

To obtain a highly efficient method for producing biallelic knockout mice, a simple computational model was first constructed to estimate the minimum efficiency of different CRISPR methods (see above for details). According to this computational model, a multiple-target CRISPR strategy, in which multiple gRNAs target the same gene, is more efficient than the high-concentration CRISPR strategy, in which a multiple-fold higher concentration of a single gRNA targets the gene of interest (A and B of FIG. 1 and A and B of FIG. 2).

In the present Example, Tyr was selected as a target gene and C57BL/6N was selected as an inbred strain. This is because the black coat color of C57BL/6N becomes white if this gene is knocked out biallelically. Three kinds of gRNAs were designed for three kinds of target sequences of the Tyr gene (gRNA1, gRNA2, and gRNA3 for targets Tyr-1, Tyr-2, and Tyr-3, respectively. C of FIG. 1 and D of FIG. 2). It was confirmed that the designed gRNAs had high cleavage efficiency (approximately 7-fold to approximately 40-fold in comparison with control) at least in cellulo by using a single strand annealing (SSA) assay (D of FIG. 1 and E of FIG. 2). In the SSA assay, the DNA cleavage made by the CRISPR/Cas9 system induced the recombination of incomplete fragments of firefly Luciferase (Luc). This resulted in an entire Luc gene and enhanced bioluminescence.

When gRNAs are injected into fertilized eggs, the single-target method using each of the three kinds of gRNAs alone at 150 ng/µl exhibited only moderate efficiency (36.0%, 54.2% and 64.7%, respectively, F of FIG. 1 and F of FIG. 2). Then, the following two parameters were estimated: (i) S(=5.72) which is an effective total gRNA concentration in comparison with the dissociation constant of gRNA and (ii) α(=0.136), which is the recovery rate of mutation, were estimated. This made it possible to predict the minimum efficacy of the triple-target CRISPR method for whole-body biallelic knockout mice as 82.6% (G of FIG. 2). In fact, the triple-target strategy using the mixture of Cas9 mRNA (100 ng/µl) and three kinds of gRNAs (gRNA1, gRNA2 and gRNA3, each at 50 ng/µl) achieved almost perfect efficiency (97.5%, E and F of FIG. 1 and H of FIG. 2). qPCR of the target sequence including the CRISPR-target sequence was performed, and it was then confirmed that five out of six CRISPR-target regions from two Tyr knockout mice were not detectable. These quantitative qPCR results matched with each other among the genomic DNAs extracted from brains, scalps and tails (H of FIG. 2). This is consistent with the observed whole-body biallelic knockout phenotype (i.e. white coat color) of Tyr gene. It should be noted that observed knockout efficacy (97.5%) is more than the predicted minimum efficiency (82.6%) (G of FIG. 2). It is speculated that the increased knockout efficiency would be the result of irreversible mutations such as deletion between multiple CRISPR target sites.

Figure 3:
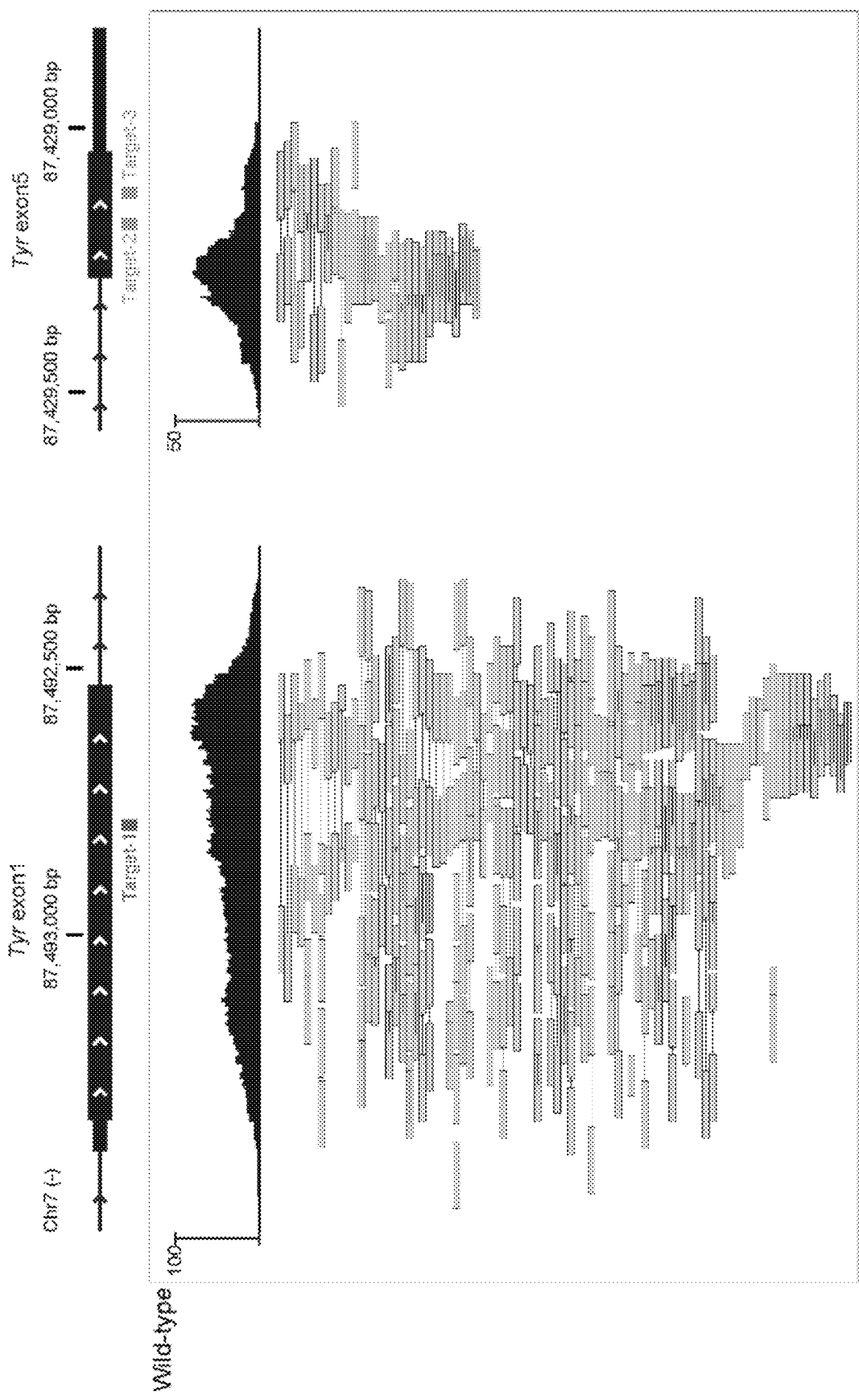
FIG. 3 shows results of exome analysis of whole-body biallelic Tyr knockout mice produced by a triple-target CRISPR method.
Figure 3:
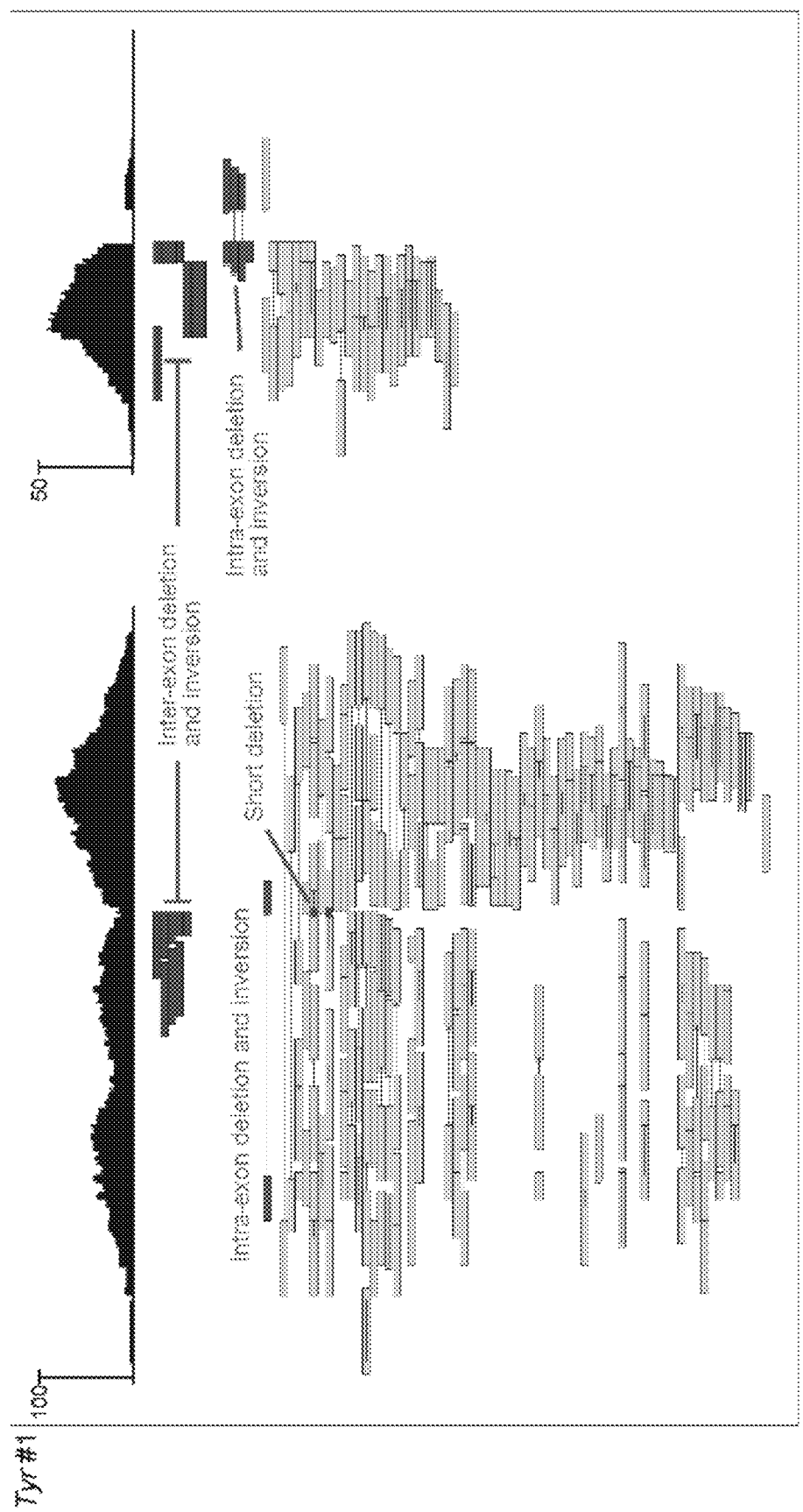
Figure 3:
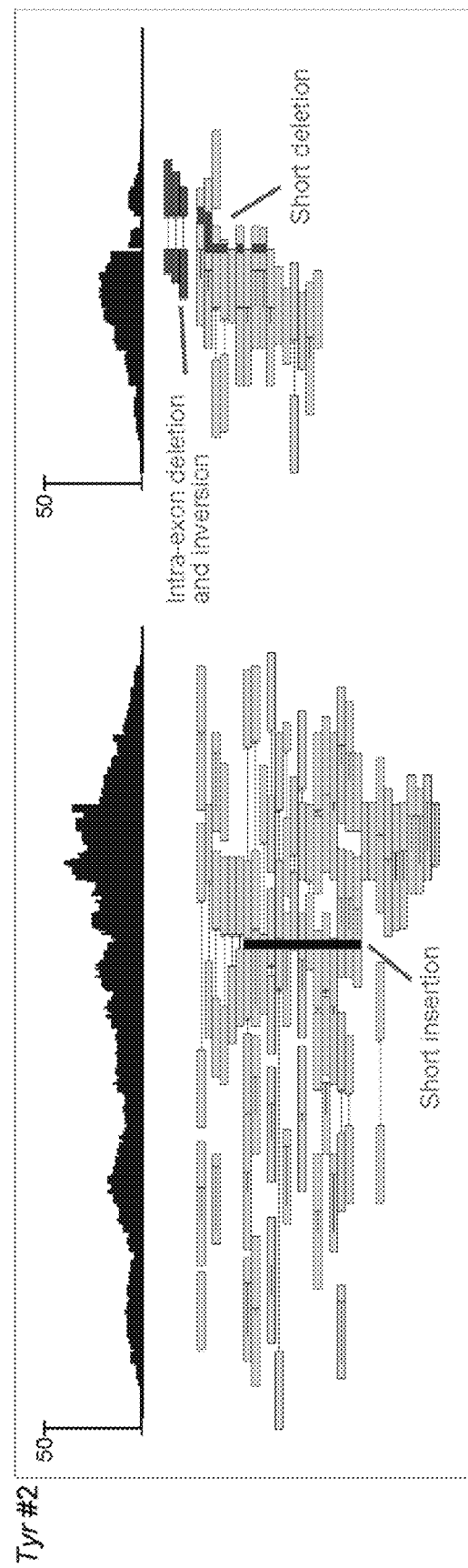

To investigate genomic effect, exome sequencing was performed. This resulted in 91.6% to 95.6% of target bases being covered more than 10 times. As a result, on-target deletions of genomic stretches having various lengths was demonstrated (FIG. 3), and no off-target mutation was demonstrated. Therefore, the triple-target CRISPR method could produce biallelic knockout mice with >90% efficiency in a single generation. Furthermore, undetectable expression of TYR protein was confirmed by mass spectrometry (MS) in comparison with another independently produced triple-target CRISPR knockout strain (FIG. 3). As has been described, a triple-target CRISPR method allowed production of biallelic knockout mice with an efficiency of more than 90% in a single generation. Since a triple-target CRISPR method achieves high efficiency (>90%) for the biallelic knockout of a single gene, a triple-target CRISPR method has a potential to achieve efficiency higher than 80% even for the biallelic knockout of dual genes. This is useful for reliable analysis of behavioral phenotypes.

(Development of Database for Publicly Available Triple-Target CRISPR Method)

As described above, triple-target CRISPR makes it possible to efficiently produce biallelic knockout mice. However, while several knockout mice were produced by use of the method, it was still time-consuming to manually design triple targets for the same gene, even with use of existing tools to (i) extract candidate target sequences for a given genome sequence (http://cas9.cbi.pku.edu.cn/index.jsp) (Ma, M., Ye, A. Y., Zheng, W., and Kong, L. (2013). A guide RNA sequence design platform for the CRISPR/Cas9 system for model organism genomes. BioMed research international 2013, 270805) and (ii) to evaluate an off-target risk for each candidate (http://tools.genome-engineering.org) (Ran, F. A., Hsu, P. D., Wright, J., Agarwala, V., Scott, D. A., and Zhang, F. (2013). Genome engineering using the CRISPR-Cas9 system. Nature protocols 8, 2281-2308.). This manual design procedure requires up to a few hours for a single gene, and therefore limits the ability to perform large-scale screenings. Therefore, an attempt was made to develop an automated method that performs all of the gRNA selection steps. The whole mouse genome was scanned, and all of the suitable targets are now in an online database (FIG. 4, see experimental protocols for details). This gRNA database provides at least three target sequences (one set for triple-target CRISPR) for 81.2% of mouse genes. In addition, 71.9% of all mouse genes have more than 6 target sequences (multiple sets for triple-target CRISPR), which are also included (B and C of FIG. 4).

To validate the usefulness of the triple-target CRISPR database, two independent sets of triple targets for the Tyr gene were selected (Tyr-4, Tyr-5, and Tyr-6 for set 2, and Tyr-7, Tyr-8, and Tyr-9 for set 3, A of FIG. 5). These sets were distinct from Tyr-1, Tyr-2, and Tyr-3 (set 1) used in the previous experiments (C of FIG. 2). When gRNAs were injected into fertilized eggs, the triple-target method using both sets of the gRNAs showed almost perfect efficiency (96.6% and 100%, respectively, D and E of FIG. 4). This supports the usefulness of the triple-target CRISPR database. This database is now public (http://crispr.riken.jp/). The instructions are summarized in FIG. 5. In brief, a user inputs a name of a gene in the search box, and then clicks "Submit" (B of FIG. 5). By selecting "Coding Region", "5'UTR", "3'UTR", or "Isoform-dependent", it is possible to select target locations of gRNAs (B of FIG. 5). Output information by default contains: target sequence; target location; target orientation; and probe locations with respect to genes. There is also optionally-selectable information such as: gRNA sequence; off-target score; and primers of targets (B of FIG. 5). The search results can be viewed in a table format, and can be downloaded on demand as a CSV file (C of FIG. 5).

<Consideration>
(Triple-Target CRISPR Enables Efficient Production of Biallelic Knockout Mice in a Single Generation.)

An object of the present invention is highly efficient (>90%) production of whole-body biallelic knockout mice in a single generation. The inventors of the present invention used a simple computational model to estimate the minimum efficiency of different CRISPR methods, and discovered that multiple-target CRISPR methods would allow production of mutant mice with much higher efficiency than that of single-target CRISPR. In the present invention, the inventors designed three different kinds of gRNAs against the Tyr gene, and, by the triple-target method using a mixture of three kinds of gRNAs (Tyr-1, Tyr-2, Tyr-3), achieved almost perfect efficiency (97.5%). Meanwhile, it was confirmed that the single-target method with any of the gRNAs at a three-fold higher concentration had merely moderate efficiency. Genomic verification revealed no off-target mutation at least in exons (FIG. 3). The total number of base pairs (bp) read in the exome sequencing (including Tyr knockout (set 1)) was 65.6 Gbp. This is more than 24 times greater than the whole genome base pairs of mouse (2.7 Gbp). This, therefore, provides sufficient coverage to be confident that off-target effect of the triple-target CRISPR strategy is not a problem in practice. Importantly, the DNA-cleavage efficiency of Tyr-3 was more than three-fold higher than that of Tyr-2 (D of FIG. 1), whereas the whole-body biallelic knockout efficiency for Tyr-3 (64.7%) was similar to that of Tyr-2 (54.2%). This indicates that a limiting factor in vivo is not DNA-cleavage by the CRISPR/Cas9 system, but other factors such as DNA repair. This is consistent with the prediction by the computational model. The reproducibility and robustness of the triple-target method were further confirmed by additional experiments in which two independent sets of three kinds of gRNAs against the Tyr gene were used (D and E of FIG. 4). The knockout efficiency was also confirmed by genotyping all mice used for the analysis in this test. 102 mice produced by the triple-target CRISPR method (including eleven single-knockout strain and two double-knockout strains were genotyped. At least 92.2% (n=94) of the animals were confirmed as knockout mice by qPCR or sequencing. This efficiency was confirmed to be higher than the minimum efficiency predicted by the model described above. In addition, a publicly available CRISPR database, from which triple-target candidate gRNAs for 81.2% or more of the genes in the mouse genome is also provided (FIG. 4).

All of the literature (the publications and the patent document) cited herein are incorporated herein by reference. Reference may be made to any literature above to understand not only the parts specifying the literature but also any matters disclosed herein.

The invention claimed is:

1. A method for producing a knockout mouse, comprising the steps of:
   obtaining an embryo in which a target gene has been knocked out by introducing a CRISPR-Cas system into a cell having one or more kinds of target genes, the CRISPR-Cas system being able to produce (i) three or more kinds of guide RNAs for each of the one or more kinds of target genes and (ii) a Cas protein; and
   transplanting the embryo into a pseudopregnant mouse, so as to obtain an offspring, wherein
   the three or more kinds of guide RNAs satisfy all of the following conditions (1) through (5):
   (1) a genome contains a single target as a target of each of the three or more kinds of guide RNAs;
   (2) a target of each of the three or more kinds of guide RNAs is neither: (i) a target with a low AT percentage below 45%, which has a risk of binding strongly to an off-target site which is a site other than an intended sequence in a target gene nor (ii) a target that contains TTTT, which tends to loosen the gRNA's secondary structure;
   (3) a target of each of the three or more kinds of guide RNAs is not excessively similar to a reverse primer in a case where PCR-based synthesis of gRNA template is performed with use of pX330 as template;
   (4) a candidate for a target of each of the three or more kinds of guide RNAs, for which candidate a stem loop structure for Cas9 recognition cannot correctly fold, is to be eliminated, except in a case where folding energy was above −18 which indicates that the "wrong" structure was very unstable as a result of calculation of a secondary structure of gRNA; and
   (5) a score of an off-target risk of a target of each of the three or more kinds of guide RNAs, which off-target risk is evaluated by using an off-target score calculating method of the CRISPR Design Tool, is 75 or more.

2. The method as set forth in claim 1, wherein
   the target gene is a biallelic gene, and
   a ratio of whole-body biallelic knockout individuals to all of offspring obtained is 90% or more.

3. The method as set forth in claim 2, wherein
   the target gene is two or more kinds of target genes, and
   a ratio of whole-body biallelic knockout individuals for each of the two or more kinds of target genes to all of offspring obtained is 90% or more.

* * * * *